US007332482B2

(12) United States Patent
Adorini et al.

(10) Patent No.: US 7,332,482 B2
(45) Date of Patent: Feb. 19, 2008

(54) METHOD FOR TREATING BENIGN PROSTATIC HYPERPLASIA

(75) Inventors: Luciano Adorini, Milan (IT); Enrico Colli, Milan (IT)

(73) Assignee: BioXell S.p.A., Milan (IT)

( * ) Notice: Subject to any disclaimer, the term of this patent is extended or adjusted under 35 U.S.C. 154(b) by 41 days.

(21) Appl. No.: 10/903,211

(22) Filed: Jul. 29, 2004

(65) Prior Publication Data

US 2005/0065124 A1 Mar. 24, 2005

(30) Foreign Application Priority Data

Sep. 24, 2003 (GB) ................................. 0322395.5
Nov. 3, 2003 (GB) ................................. 0325598.1

(51) Int. Cl.
*A61K 31/593* (2006.01)
*A61K 31/59* (2006.01)

(52) U.S. Cl. ...................... 514/167; 552/653

(58) Field of Classification Search ................. 514/167; 552/653
See application file for complete search history.

(56) References Cited

U.S. PATENT DOCUMENTS

| 5,747,479 | A | 5/1998 | Bryce et al. |
| 5,763,429 | A | 6/1998 | Bishop et al. |
| 5,795,882 | A | 8/1998 | Bishop et al. |
| 5,804,574 | A | 9/1998 | Bryce et al. |
| 5,811,414 | A | 9/1998 | Bryce et al. |
| 5,872,113 | A | 2/1999 | Nestor, Jr. et al. |
| 5,939,408 | A | 8/1999 | Batcho et al. |
| 6,008,209 | A | 12/1999 | Manchand et al. |
| 6,030,963 | A | 2/2000 | Iacobelli et al. |
| 6,331,642 | B1 | 12/2001 | Batcho et al. |
| 2002/0128240 | A1 | 9/2002 | Mazess |

FOREIGN PATENT DOCUMENTS

| EP | 0 808 833 | 11/1997 |
| EP | 0654467 | 2/1998 |

(Continued)

OTHER PUBLICATIONS

Mealy, N E: "BXL-268" Drugs of the Future 2004 Spain, vol. 29, No. 6, p. 629.
Anon: Drug News and Perspectives, 2003, vol. 16. No. 2, p. 122.
Brandl, M. et al. J. Pharmaceutical Sciences. 2003, 92, p. 1981-1989.
Crescioli, C. et al. European J. Endocrinology. 2004, 150, p. 591-603.
C. Crescioli et al. Endocrinology (2003), 144(7), 3046-3057.
C. Crescioli et al. Molecular and Cellular Endocrinology (2002), 198, 69-75.
D. Villari et al. Journal of Urology (2003), 169(4) Suppl 281.
A. Krishnan et al. Journal of Cellular Biochemistry (2003), 88(2), 363-371.
C. Crescioli et al. Journal of Clinical Endocrinology and Metabolism (2000), 85(7), 2576-2583.
H. Huynh et al. International Journal of Oncology (1998), 13(1), 137-143.
G. Schwartz et al. Cancer Epidemiology, Biomarkers and Prevention (1998), 7(5), 391-395.
D. Feldman et al. Advances in Experimental Medicine and Biology (1995), 375, 53-63.
D. Kirk. International Journal of Cancer Supplement (2002) 13, 54.
A. Ismail et al. Journal of Bone and Mineral Research (2002), 17(1), S288.
A. Ismail et al. Journal of Bone and Mineral Research (2001), 16(1), S429.
S. Peleg et al. Bone (New York) (2000), 27(4) 29S.
S. Tong et al. Journal of Bone and Mineral Research (2000), 15(1), S562.
S. Peleg et al. Journal of Cellular Biochemistry (2003) 88(2), 267-273.
S. Peleg et al. Endocrinology (2002), 143 (5), 1625-1636.
M. Kabat et al. Journal of Organic Chemistry (2001), 66(18), 6141-6150.
M. Brandl et al. Journal of Pharmaceutical Sciences, 92(10), 2003, 1981-1989.
H. Dallosso et al. Neurourology and Urodynamics (2004) 23, 204-210.
B. Konety et al. Journal of Urology (2001) 165, 253-258.
C. Crescioli et al. European Journal of Endocrinology (2004) 150:591-603.
J. Hsu et al. Cancer Research (2001) 61(7):2852-2856.
M. Campbell et al. Journal of the National Cancer Institute (1997) 89(3):182-184.
I. Thompson et al. New England Journal of Medicine (2003) 349(3): 215-224.
V. Kassabian. The Lancet (2003) 361: 60-62.
P. Scardino. New England Journal of Medicine (2003) 349(3): 297-299.
M. Brandl et al. Journal of Pharmaceutical Sciences (2003) 92(10): 1981-1989.
Marco Marcelli, et al., "Hormonal Signaling in Prostatic Hyperplasia and Neoplasia," The Journal of Clinical Endocrinology & Metabolism, vol. 84, No. 10, pp. 3463-3468 (1999).
Feldman, Glorieux and Pike, Chapter 62, "The 16-Ene Vitamin D Analogs", of *Vitamin D*, pp. 1045-1060 (1997).

(Continued)

*Primary Examiner*—Sabiha N. Qazi
(74) *Attorney, Agent, or Firm*—Edwards Angell Palmer & Dodge LLP; Peter C. Lauro, Esq.

(57) ABSTRACT

The use of 1-alpha-fluoro-25-hydroxy-16,23E-diene-26,27-bishomo-20-epi-cholecalciferol, or a pharmaceutically acceptable salt or ester thereof, for the manufacture of a medicament for the prevention and/or treatment of benign prostatic hyperplasia (BPH) and associated symptoms.

16 Claims, 17 Drawing Sheets

| | FOREIGN PATENT DOCUMENTS | |
|---|---|---|
| EP | 1048661 | 11/2000 |
| EP | 0980354 | 6/2002 |
| EP | 808832 | 4/2003 |
| EP | 1 082 298 | 11/2003 |
| EP | 1050537 | 11/2003 |
| EP | 0 808 833 | 9/2004 |
| IT | 1297381 | 12/1997 |
| WO | WO 97/25050 | 7/1997 |
| WO | WO-98/29123 A1 | 7/1998 |
| WO | WO 01/30751 | 5/2001 |
| WO | WO 03/032961 | 4/2003 |
| WO | WO-03/034961 A1 | 5/2003 |
| WO | WO-03/047595 A1 | 6/2003 |

OTHER PUBLICATIONS

M. Maggi, et al., "Pre-clinical Evidence and Clinical Translation of Benign Prostatic Hyperplasia Treatment by the Vitamin D Receptor Agonist BXL-628 (Elocalcitol)." *J. Endocrinol. Invest.* 29: 665-674 (2006).

FIGURES

METHOD FOR TREATING BENIGN PROSTATIC HYPERPLASIA

RELATED APPLICATIONS

This application claims priority to GB 0322395.5, filed Sep. 24, 2003, and to GB 0325598.1, filed Nov. 3, 2003, both of which applications are incorporated herein in their entireties by this reference.

FIELD OF THE INVENTION

The present invention is concerned with the use of 1-alpha-fluoro-25-hydroxy-16,23E-diene-26,27-bishomo-20-epi-cholecalciferol (Compound A) for the manufacture of a medicament for the prevention and/or treatment of benign prostatic hyperplasia (BPH) and associated symptoms. It is further concerned with a method for preventing and/or treating benign prostatic hyperplasia and associated symptoms by administering 1-alpha-fluoro-25-hydroxy-16,23E-diene-26,27-bishomo-20-epi-cholecalciferol in an amount effective to prevent and/or to treat such disease alone or in combination with further active agents.

BACKGROUND OF THE INVENTION

BPH is a common disorder in elderly men, occurring in approximately 50% of men aged 60 years and in 90% of those aged 85 years. BPH is a specific histopathological entity characterized by stromal and epithelial cell hyperplasia.

For over a century, the two known etiologic factors for the pathogenesis of BPH have been aging and the presence of functional testes. However, as the science of prostate biology advances, this concept becomes inadequate as it does not cover all aspects of BPH pathogenesis. Additional etiologic factors play a significant role in regulating prostatic growth. In particular, evidence has emerged that prostatic growth is under the immediate control of specific growth factors produced by prostatic cells, acting locally on adjacent cells in a paracrine mechanism or to the same cells in an autocrine mechanism. Therefore much effort is currently being put into identifying therapeutic strategies aimed at inhibiting intraprostatic growth factors.

BPH is a common cause of chronic lower urinary tract symptoms which may affect both the filling (irritative symptoms) and voiding (obstructive symptoms) phases of the micturition cycle. These symptoms affect the social, psychological, domestic, occupational, physical and sexual lives of the patients leading to a profound, negative impact on their quality of life. In addition to this, BPH can cause more acute urological complications, particularly acute urinary retention (AUR), often considered the most serious complication of BPH and less frequently recurrent urinary tract infections, upper urinary tract dilatation, bladder stone formation and recurrent hematuria.

BPH management is associated with extremely high social costs, estimated to be 4 billion dollars in 1993 and projected to be 26 billion dollars in 2003 in the USA alone.

The current medical treatment for BPH consists of orally administered 5 alpha reductase inhibitors (finasteride and dutasteride, recently approved by the FDA) and alpha 1 receptor antagonists (terazosin, doxazosin, tamsulosin as well as silodosin, AIO-8507L, RBx-2258 etc). Each of these therapeutic options is associated with both advantages and disadvantages relating to their different mechanisms of action. Although alpha 1 receptor antagonists are very effective in reducing symptoms related to lower urinary tract symptoms (LUTS), they are ineffective in reducing the prostate volume and therefore in preventing BPH-related surgery. Conversely, 5 alpha reductase inhibitors like finasteride and dutasteride, by decreasing dihydrotestosterone (DHT) formation, reduce prostate size and the need for surgery.

In addition, recent results from the seven-year Prostate Cancer Prevention Trial, involving more than 18.000 healthy aged man, demonstrated that finasteride can prevent or delay the appearance of prostate cancer (see Thompson I M, et al. *New England Journal of Medicine* (2003) 349 p 215-224). However, as expected (see Kassabian V S, *Lancet* (2003) 361 p 60-62), finasteride was not free from anti-androgenic adverse effects on sexual function, such as decreased sexual potency, sexual desire and gynecomastia, that substantially lessen its attractiveness as a cancer-preventing agent. In addition, finasteride treatment was associated with an increased detection of high-grade prostate cancer, probably because the finasteride-induced low androgen state selected the most aggressive, androgen-insensitive malignant growing cells (see Scardino P T, *New England Journal of Medicine* (2003) 349 p 297-299).

Thus there is an unmet need for a new class of drugs for medical therapy of BPH, which should be able to prevent acute urinary retention, together with its related need for surgery, by decreasing androgen-induced prostate growth but without directly interfering with androgen receptors (AR), and therefore without anti-androgenic prostatic and extra-prostatic adverse effects, for example, sexual side effects. Such medicaments, by disrupting intra-prostatic growth factor signalling, might be useful not only for treating BPH but also for preventing prostate cancer, possibly without selecting AR-insensitive, malignant clones.

SUMMARY OF THE INVENTION

As described herein, the Inventors have determined that the non-hypercalcemic, well-tolerated, vitamin $D_3$ analogue 1-alpha-fluoro-25-hydroxy-16,23E-diene-26,27-bishomo-20-epi-cholecalciferol (Compound A), is a primary example of such a medicament, as it can act against BPH in an androgen-receptor independent manner by targeting multiple pathways controlling BPH cell growth, including growth factor-mediated prostate proliferation.

1,25-dihydroxyvitamin $D_3[1,25(OH)_2D_3]$, the activated form of vitamin $D_3$, is a secosteroid hormone that not only plays a central role in bone and calcium metabolism, but is also involved in the regulation of the immune response and the differentiation and apoptosis of many cell types, including malignant cells.

However, a problem with the therapeutic use of calcitriol is its natural ability to induce hypercalcemia and hyperphosphatemia. Hence, analogues of calcitriol retaining biological activity but devoid of hypercalcemic side effects, have been developed.

U.S. Pat. No. 5,939,408 and EP808833 disclose a number of $1,25(OH)_2D_3$ analogues including the compound 1-alpha-fluoro-25-hydroxy-16,23E-diene-26,27-bishomo-20-epi-cholecalciferol (Compound A). U.S. Pat. No. 5,939,408 and EP808833 disclose that the compounds induce differentiation and inhibition of proliferation in various skin and cancer cell lines and are useful for the treatment of hyperproliferative skin diseases such as psoriasis, neoplastic diseases such a leukemia, breast cancer and sebaceous gland diseases such as acne and seborrheic dermatitis and osteoporosis.

It has now surprisingly been found in several studies conducted by the Inventors that, unlike certain other 1,25(OH)$_2$D$_3$ analogues, the 1,25(OH)$_2$D$_3$ analogue Compound A:

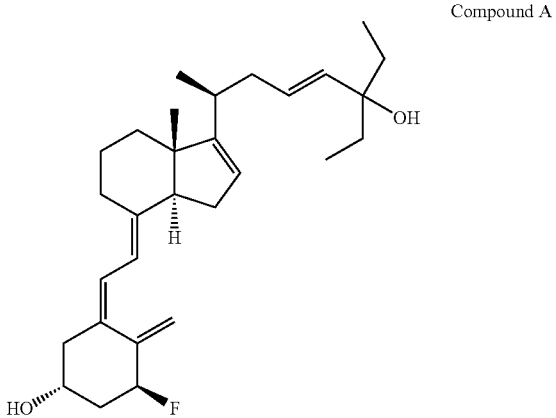

Compound A significantly reduces the growth of human BPH cells in vitro via induction of their apoptosis and reduces prostatic growth in vivo, with no effects on testosterone and dihydrotestosterone levels. Furthermore, this inhibition of prostate growth is achieved at non-hypercalcemic doses. Thus, Compound A is an effective pharmacologic agent for the treatment of benign prostatic hyperplasia.

As described in the Examples herein, Compound A reduces prostate size. Furthermore, as observed with finasteride, Compound A counteracts against the in vitro and in vivo proliferative activity of testosterone. Significantly however, and unlike finasteride, Compound A does not inhibit type-1 or type-2 5 alpha-reductase activity and can counteract not only testosterone but even dihydrotestosterone induced BPH cell growth. These anti-androgenic properties of Compound A are independent from interaction with the AR, as shown by the failure of Compound A both to bind to the AR, or to act as an AR agonist or antagonist. Furthermore, Compound A does not affect sex hormone secretion. Furthermore, in our studies, Compound A has no significant effect on PSA levels thus there appears to be no danger of treatment with Compound A masking this important indicator of possible prostate cancer.

A further significant advantage of Compound A is that in vitro studies have revealed that this drug, unlike finasteride, is capable of inhibiting the basal and testosterone-stimulated growth of bladder cells and is expected to be useful in preventing and/or treating of bladder dysfunction in humans. In vivo studies in a validated rat bladder outlet obstruction model of bladder dysfunction have also demonstrated the beneficial effect of Compound A. This is significant because bladder dysfunction is a common and troublesome sequela of BPH. Thus Compound A is capable of reducing prostate size and ameliorating bladder dysfunction, i.e., improving bladder function and bladder related symptoms of BPH at the same time through direct effect of Compound A both on the prostate and on the bladder. This effect is expected to go beyond the improvement in bladder symptoms that would be expected merely as a result of prostate size reduction. Bladder symptoms include overactive bladder and indicators of improved bladder function include reduction in non-voiding contractions and residual urine.

Thus, the present invention provides the use of 1-alpha-fluoro-25-hydroxy-16,23E-diene-26,27-bishomo-20-epi-cholecalciferol in the manufacture of a medicament for the prevention and/or treatment of benign prostatic hyperplasia. Also considered within the scope of the invention are pharmaceutically acceptable esters and salts of compound A.

The invention thus provides the use of 1-alpha-fluoro-25-hydroxy-16,23E-diene-26,27-bishomo-20-epi-cholecalciferol, or a pharmaceutically acceptable salt or ester thereof, in the manufacture of a medicament for the prevention and/or treatment of benign prostatic hyperplasia The invention also provides a method for preventing and/or treating benign prostatic hyperplasia, in patients in need of such prevention or treatment comprising administering a therapeutically effective amount of 1-alpha-fluoro-25-hydroxy-16,23E-diene-26,27-bishomo-20-epi-cholecalciferol or a pharmaceutically acceptable salt or ester thereof.

The invention also provides the use of 1-alpha-fluoro-25-hydroxy-16,23E-diene-26,27-bishomo-20-epi-cholecalciferol, or a pharmaceutically acceptable salt or ester thereof, for the prevention and/or treatment of benign prostatic hyperplasia.

The invention also provides 1-alpha-fluoro-25-hydroxy-16,23E-diene-26,27-bishomo-20-epi-cholecalciferol, or a pharmaceutically acceptable salt or ester thereof, for use in the prevention and/or treatment of benign prostatic hyperplasia.

The invention also provides the use of 1-alpha-fluoro-25-hydroxy-16,23E-diene-26,27-bishomo-20-epi-cholecalciferol, or a pharmaceutically acceptable salt or ester thereof, for the prevention and/or treatment of benign prostatic hyperplasia without anti-androgenic prostatic and extra-prostatic adverse effects. It also provides a method for preventing and/or treating benign prostatic hyperplasia without anti-androgenic prostatic and extra-prostatic adverse effects, in patients in need of such prevention or treatment, comprising administering a therapeutically effective amount of 1-alpha-fluoro-25-hydroxy-16,23E-diene-26,27-bishomo-20-epi-cholecalciferol or a pharmaceutically acceptable salt or ester thereof.

The invention also provides the use of 1-alpha-fluoro-25-hydroxy-16,23E-diene-26,27-bishomo-20-epi-cholecalciferol, or a pharmaceutically acceptable salt or ester thereof, for the prevention and/or treatment of benign prostatic hyperplasia together with concurrent prevention and/or treatment of bladder dysfunction. It also provides a method for preventing and/or treating benign prostatic hyperplasia with concurrent prevention and/or treatment of bladder dysfunction, in patients in need of such prevention or treatment, comprising administering a therapeutically effective amount of 1-alpha-fluoro-25-hydroxy-16,23E-diene-26,27-bishomo-20-epi-cholecalciferol or a pharmaceutically acceptable salt or ester thereof.

DETAILED DESCRIPTION OF THE INVENTION

Figure 1A:
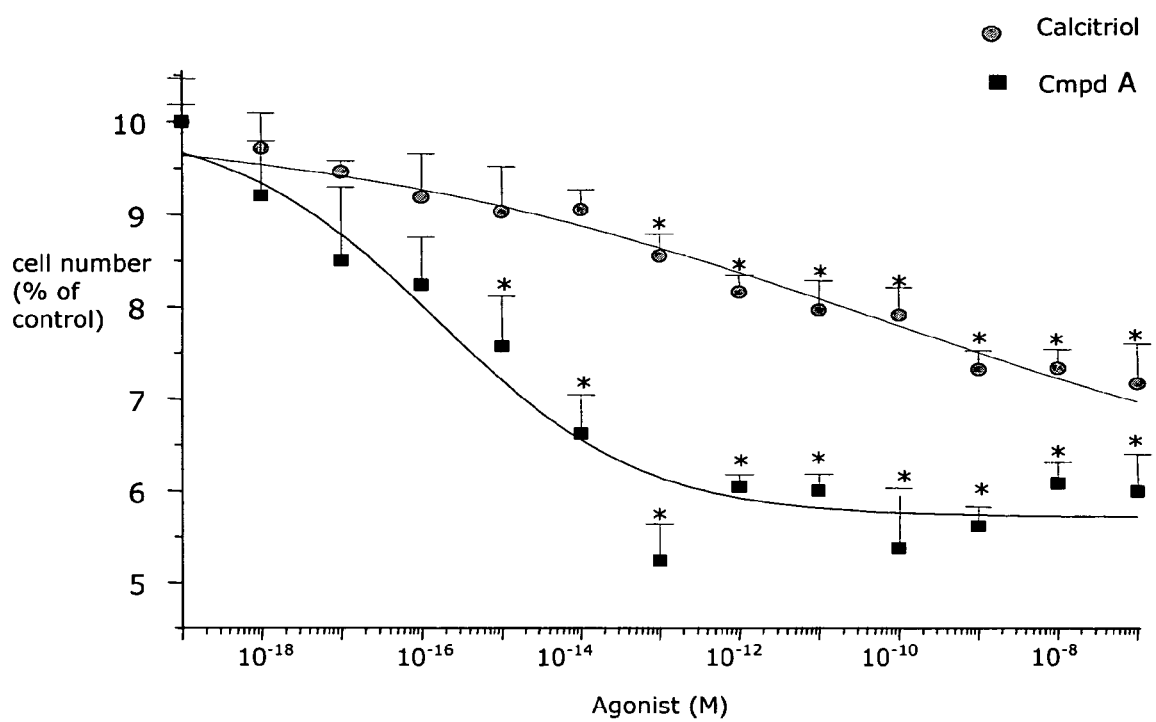
FIG. 1 shows inhibition of BPH cell proliferation by calcitriol and Compound A ("Cmpd A").

1-Alpha-fluoro-25-hydroxy-16,23E-diene-26,27-bishomo-20-epi-cholecalciferol is a known compound and its preparation is described in U.S. Pat. No. 5,939,408, the description of which is incorporated herein by reference.

Esters Include Pharmaceutically Acceptable Labile Esters That May be Hydrolysed in the Body to Release Compound A.

Salts of Compound A include adducts and complexes that may be formed with alkali and alkaline earth metal ions and metal ion salts such as sodium, potassium and calcium ions and salts thereof such as calcium chloride, calcium malonate and the like.

Compound A, or salt or ester thereof, can be used as a monotherapy or it can be administered in combination with known BPH-active agents, for example an alpha-adrenergic receptor blocking agent such as an alpha 1 receptor antagonist (for example terazosin, doxazosin or tamsulosin or else silodosin, AIO-8507L or RBx-2258) or a 5 alpha-reductase inhibitor (for example finasteride or dutasteride). The expression "BPH-active agent" includes those agents capable of or known to have activity in treating or preventing BPH such as the aforementioned example substances. The combination partner can be admixed with the compound A or its salts or esters in various ratios and can be administered separately, sequentially or simultaneously in separate or combined pharmaceutical formulations. Appropriate doses of known therapeutic agents will be readily appreciated by those skilled in the art. Combination of A with two or more, e.g., 3 BPH-active compounds may be envisaged, e.g.,combination with an alpha 1 receptor antagonist and a 5 alpha-reductase inhibitor. When administered in combination with Compound A (or salt or ester) the combination partner(s) may be used at lower doses compared to that used when the combination partner is administered alone, perhaps even a dose which is sub-therapeutic when administered alone.

Thus the invention also provides the use as defined above wherein the medicament is administered separately, sequentially or simultaneously in separate or combined pharmaceutical formulations with a second BPH-active agent.

Thus the invention also provides the use of 1-alpha-fluoro-25-hydroxy-16,23E-diene-26,27-bishomo-20-epi-cholecalciferol, or a pharmaceutically acceptable salt or ester thereof, in combination with a second BPH-active agent in the manufacture of a medicament for the prevention and/or treatment of benign prostatic hyperplasia.

The invention also provides a method for preventing and/or treating benign prostatic hyperplasia, in patients in need of such prevention or treatment comprising administering a therapeutically effective amount of 1-alpha-fluoro-25-hydroxy-16,23E-diene-26,27-bishomo-20-epi-cholecalciferol or a pharmaceutically acceptable salt or ester thereof separately, sequentially or simultaneously in separate or combined pharmaceutical formulations with a second BPH-active agent.

The combinations referred to above may conveniently be presented for use in the form of a pharmaceutical formulation. The pharmaceutical formulations thus produced also represent a further aspect of the invention.

Dosage levels and time course of administration of the active ingredients in the pharmaceutical formulations of the invention may be varied so as to obtain an amount of the active ingredient which is effective to achieve the desired therapeutic response for a particular patient, composition, and mode of administration, without being toxic to the patient. An exemplary dose range of Compound A is from 0.1 to 300 µg per day, for example 50-150 µg per day, e.g., 75 or 150 µg per day. A unit dose formulation preferably contains 50-150 µg, e.g., 75 or 150 µg and is preferably administered once per day.

Specifically, a preferred dose of Compound A is the maximum that a patient can tolerate and not develop hypercalcemia or other undesirable side effects such as hypercalcuria. Preferably Compound A is administered at a concentration of about 0.001 µg to about 100 µg per kilogram of body weight, about 0.001-about 10 µg/kg or about 0.001 µg-about 100 µg/kg of body weight. Ranges intermediate to the above-recited values are also intended to be part of the invention.

As noted above, Compound A may be administered as a pharmaceutically acceptable salt or ester thereof however preferably Compound A is employed as is, i.e., it is not employed as an ester or a salt thereof.

This dosage may be delivered in a conventional pharmaceutical formulation by a single administration, by multiple applications, or via controlled release, as needed to achieve the most effective results, preferably once or twice daily (especially once daily), e.g., by mouth. In certain situations, alternate day dosing may prove adequate to achieve the desired therapeutic response.

The selection of the exact dose and formulation and the most appropriate delivery regimen will be influenced by, inter alia, the pharmacological properties of the formulation, the nature and severity of the condition being treated, and the physical condition and mental acuity of the recipient.

Representative delivery regimens include oral, parenteral (including subcutaneous, intramuscular and intravenous), rectal, buccal (including sublingual), pulmonary, transdermal, and intranasal, most preferably oral. Administration may be continuous or intermittent (e.g., by bolus injection).

The invention also provides a pharmaceutical composition comprising 1-alpha-fluoro-25-hydroxy-16,23E-diene-26,27-bishomo-20-epi-cholecalciferol, or a pharmaceutically acceptable salt or ester thereof, and a pharmaceutically acceptable carrier for the prevention and/or treatment of benign prostatic hyperplasia.

The invention also provides a packaged formulation which includes a pharmaceutical composition comprising 1-alpha-fluoro-25-hydroxy-16,23E-diene-26,27-bishomo-20-epi-cholecalciferol, or a pharmaceutically acceptable salt or ester thereof, and a pharmaceutically-acceptable carrier packaged with instructions for use in the treatment of benign prostatic hyperplasia.

As mentioned above, such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; Pharmaceutical Technology, 9, (1985)). Some of the advantages of using SEG capsules are: a) dose-content uniformity is optimized in SEG capsules because the drug is dissolved or dispersed in a liquid that can be dosed into the capsules accurately; b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area; and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

In an example formulation, the soft gelatin capsules are size 2, white, opaque, oval gelatin capsules containing a liquid fill consisting of the active ingredient, Compound A, dissolved in Miglyol 812 (triglyceride of fractionated $C_8$-$C_{12}$ coconut oil fatty acids) with butylated hydroxytoluene (BHT), and butylated hydroxyanisole (BHA), as preservatives. The soft gelatin capsules can be formulated to contain between 0.01 and 25 mg, e.g., 75 or 150 μg of Compound A. Soft gelatin capsules should be stored at 2-8° C. and protected from light.

Formulations containing Compound A, or a pharmaceutically acceptable salt or ester thereof, optionally in combination with a second BPH-active agent, may be prepared by mixing the ingredients.

Formulations are Preferably Prepared Under Nitrogen in Amber Light.

EXAMPLES

Figure 1B:
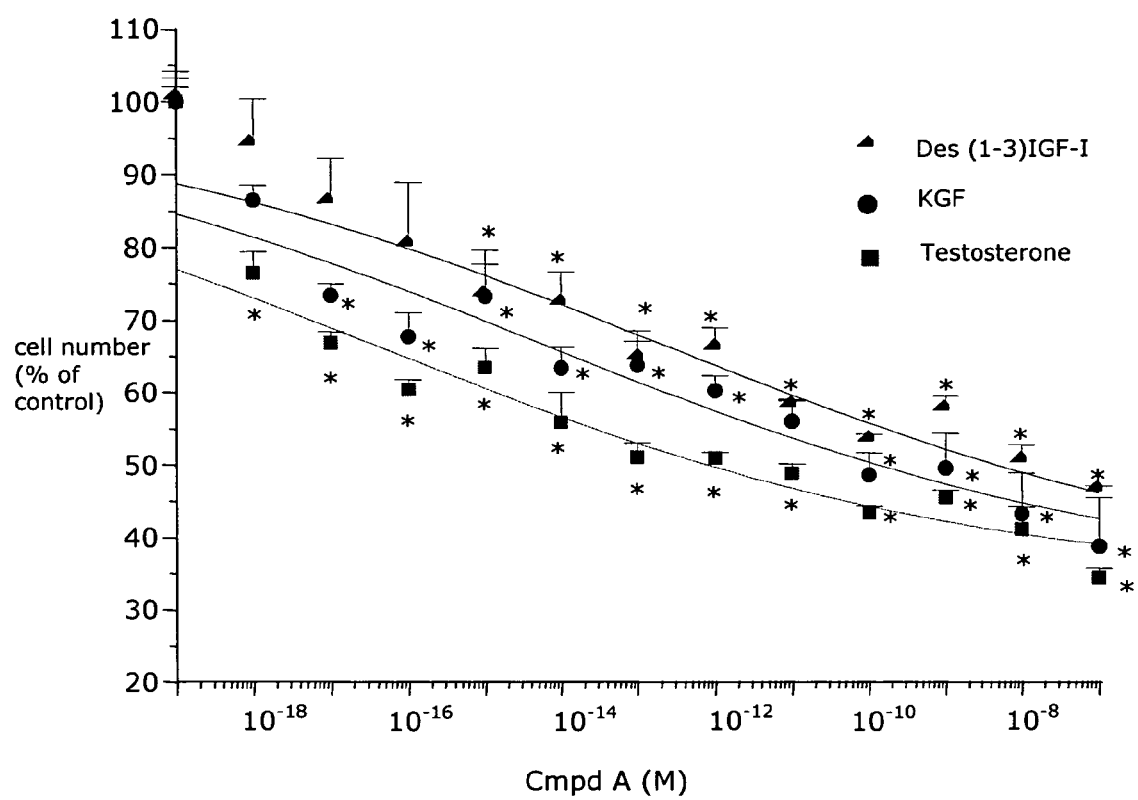

The present invention will now be described with reference to the following non-limiting examples, with reference to the figures, in which:

FIG. 1 shows inhibition of BPH cell proliferation by calcitriol and Compound A ("Cmpd A"). Panel A Incubation for 48 h with increasing concentrations ($10^{-18}$-$10^{-7}$ M) of calcitriol (circles) or Compound A (squares) resulted in a significant and dose-dependent inhibition of BPH cell growth (*P<0.01 vs control). ALLFIT analysis indicates that the two secosteroids share the same maximal inhibition ($I_{max}$=43±1%), but show a marked difference in the rank of potency (−log $IC_{50}$ Compound A=15.8±0.3; −log $IC_{50}$ calcitriol=10.2±0.6, P<0.005). Results are expressed as % inhibition (mean±SEM) over their relative controls in 3 different experiments performed in triplicate. Panel B Effect of increasing concentrations ($10^{-18}$-$10^{-7}$ M) of Compound A on BPH cell proliferation stimulated by T (10 nM, squares), KGF (10 ng/ml, circles) or Des(1-3)IGF-I (10 ng/ml, triangles). Compound A induced a significant inhibition (*P<0.01 vs T- or GF-treated cells) of BPH cell growth also in presence of all the stimuli tested with similar $I_{max}$=66.6±7.3%. However, Compound A was more potent in inhibiting the effect of T (−log $IC_{50}$=16.4±0.6), than of the other two GFs, (−log $IC_{50}$ Des(1-3)IGF-I=12.7±0.6, and −log $IC_{50}$ KGF=14.2±0.6, P<0.0001). Results are expressed as % variation (mean±SEM) over the maximal stimulation in 3 different experiments performed in triplicate.

Figure 2A:
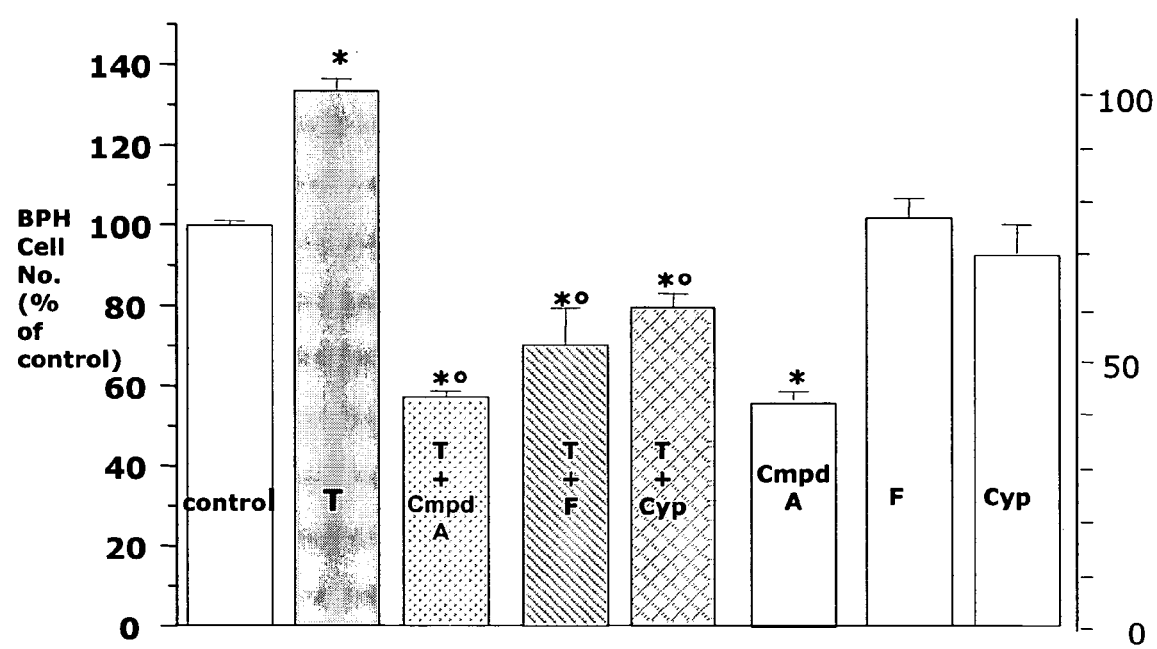
FIG. 2 shows the effect of Compound A, cyproterone acetate and finasteride on androgen-stimulated BPH cell growth.
Figure 2B:
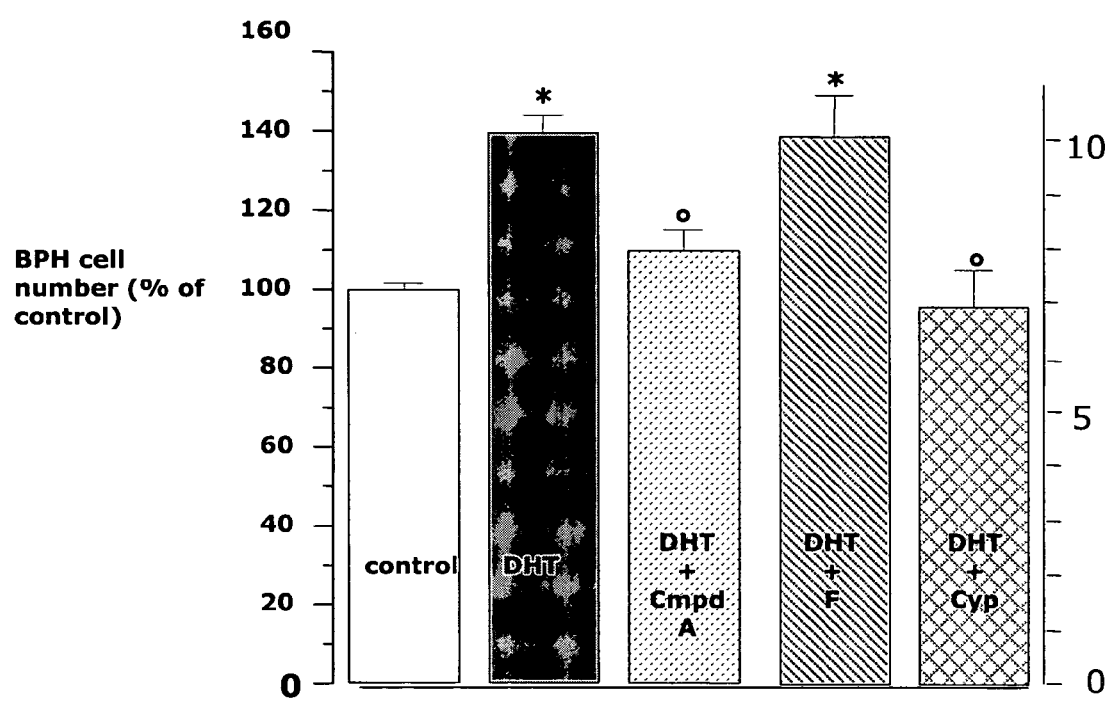

FIG. 2 shows the effect of Compound A, cyproterone acetate and finasteride on androgen-stimulated BPH cell growth. BPH cells were incubated for 48 h with Compound A (1 nM) or anti-androgens (finasteride, F, 1 nM; cyproterone acetate, Cyp, 100 nM) in the presence of T (10 nM, Panel A) or DHT (10 nM, Panel B). Results obtained in unstimulated BPH cells are also shown (Panel A). Results are expressed as % variation (mean±SEM) over their relative controls in three different experiments performed in quadruplicate. Compound A and cyproterone acetate significantly blocked both T- and DHT-induced growth, while finasteride was effective only against T. *P<0.01 vs control; °P<0.01 vs androgen-treated cells.

Figure 3A:
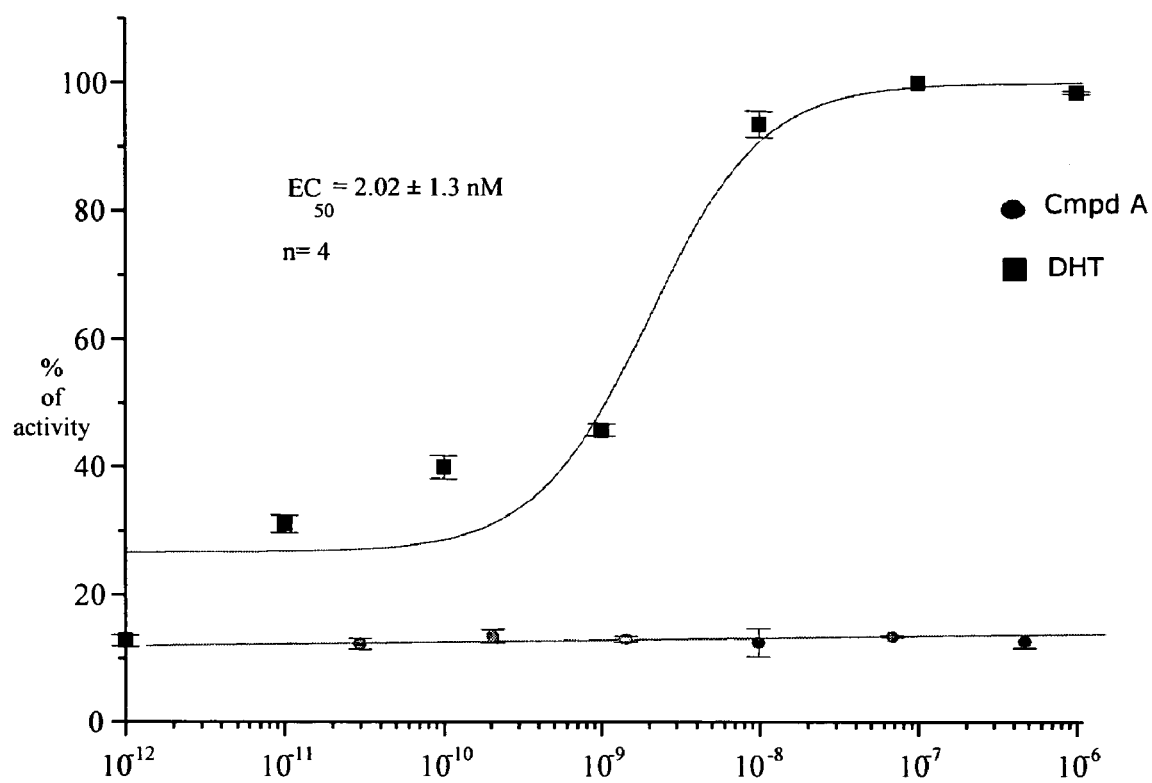
FIG. 3 shows the lack of agonistic or antagonistic properties of Compound A on human AR.
Figure 3B:
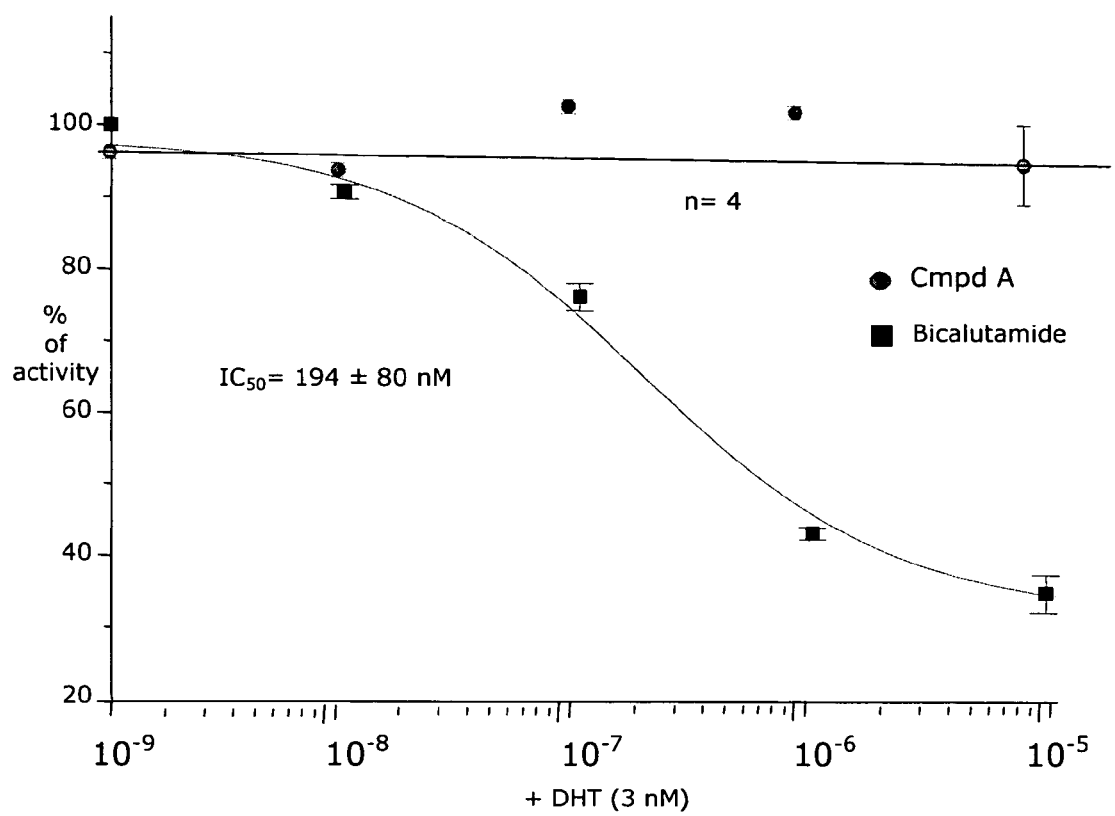

FIG. 3 shows the lack of agonistic or antagonistic properties of Compound A on human AR. The AR deficient PC3 cell line stably transfected with the human AR was plated in 24 well plates at a density of $2\times10^4$ cells/well. After 24 h, the cells were transfected with the AR-responsive plasmid pLSPP and, 48 h later, cells were incubated with increasing concentrations of DHT (squares) or Compound A (circles) (panel A), or with a fixed concentration of DHT (3 nM) in the presence of bicalutamide (squares) or Compound A (circles)(panel B) for 18 h. Results (the mean of three transfection experiments) are expressed as percentage of bioluminescence per μg of total proteins. To evaluate agonistic activity 100% luciferase activity was set in the presence of DHT 100 nM (panel A), whereas to test antagonistic activity 100% luciferase activity was set with DHT 3 nM (panel B).

Figure 4A:
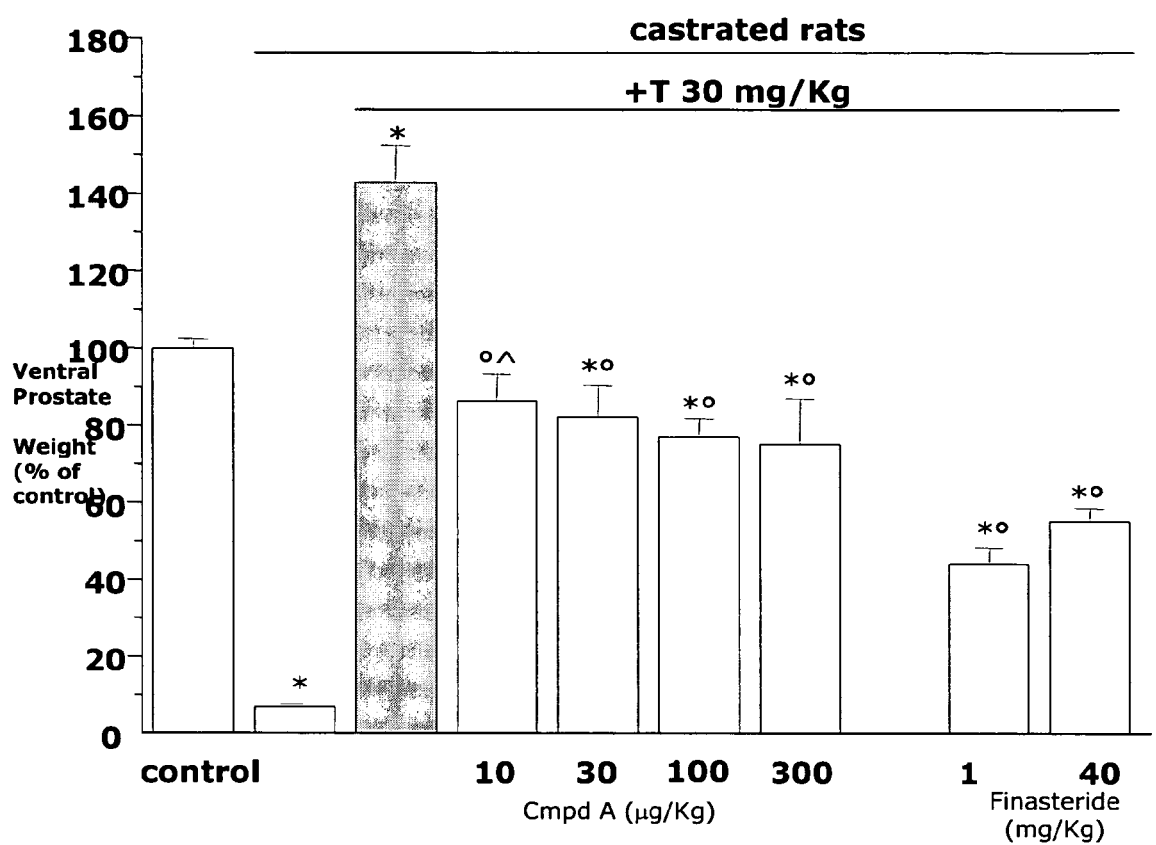
FIG. 4 shows inhibition of rat ventral prostate growth by Compound A or finasteride.
Figure 4B:
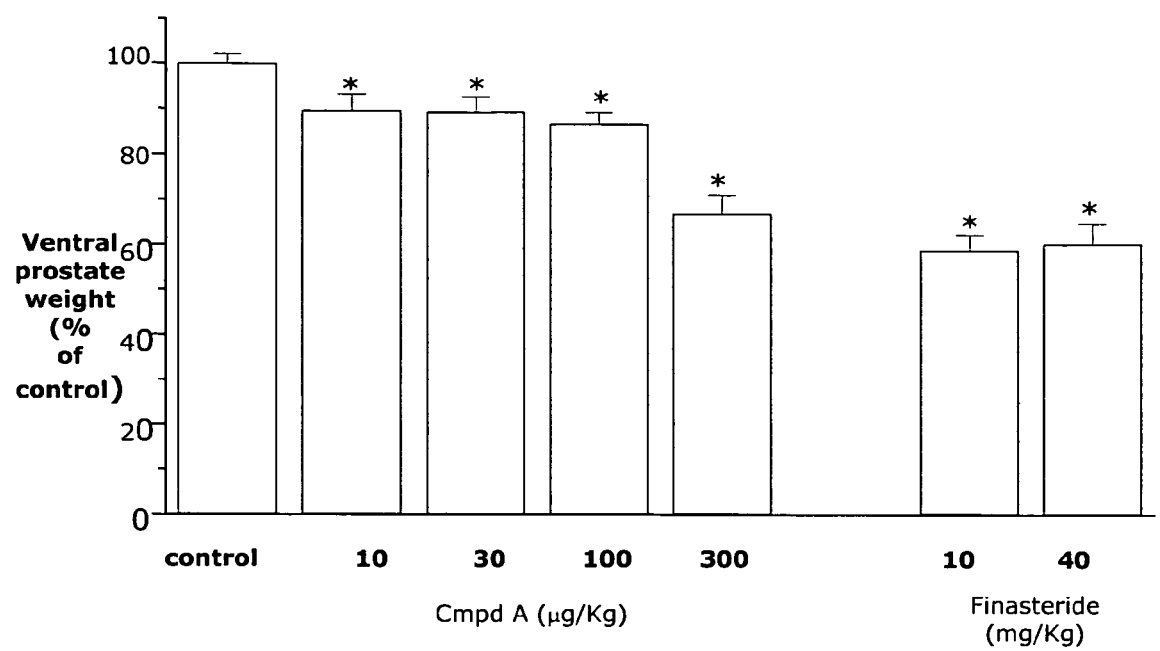

FIG. 4 shows inhibition of rat ventral prostate growth by Compound A or finasteride. Panel A: Castrated rats, injected with T enanthate (30 mg/Kg/week), were orally treated for 5 day/week for two consecutive weeks with vehicle or with increasing doses of Compound A (10, 30, 100 and 300 μg/Kg) or finasteride (F, 10 and 40 mg/Kg). Ventral prostate weight is expressed as % variation (mean±SEM) of the weight of intact, vehicle-treated, rats (^P<0.05, *P<0.01 vs control rats, °P<0.01 vs T-supplemented rats). Panel B: Intact adult rats were orally treated for over one month (5 times/week for a total of 27 administration) with vehicle (control) or increasing concentrations of Compound A (10, 30, 100 and 300 μg/Kg) or finasteride (F, 10 and 40 mg/Kg). Ventral prostate weight is expressed as % variation (mean±SEM) of the weight of control, vehicle-treated rats (*P<0.01 vs control rats).

Figure 5:
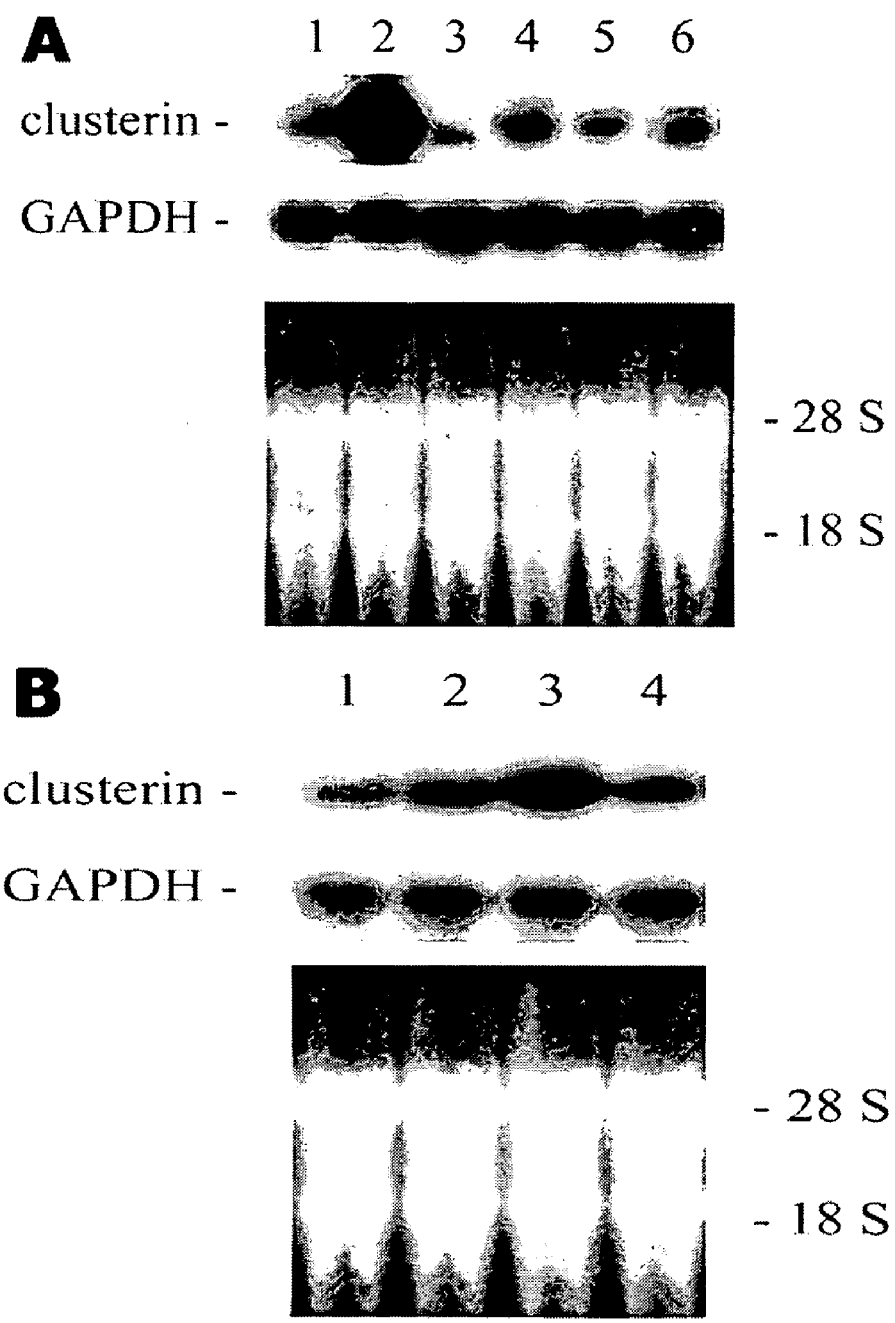
FIG. 5 shows the effect of Compound A and finasteride on clusterin gene expression in the rat ventral prostate.

FIG. 5 shows the effect of Compound A and finasteride on clusterin gene expression in the rat ventral prostate. Panel A. Northern analysis of clusterin mRNA expression in the ventral prostate of vehicle-treated intact (lane 1) or orchidectomized (lane 2) rats. Lanes 3-6 show clusterin gene expression in orchidectomized rats supplemented for two weeks with T enanthate (30 mg/Kg) and orally treated with vehicle (lane 3), Compound A (300 μg/Kg, lane 4 and 100 μg/Kg, lane 5) or finasteride (40 mg/Kg, lane 6). Every lane was loaded with 10 μg of total RNA. The corresponding GAPDH expression and the ethidium bromide staining of the gel are shown below the blot. The blot is representative of two separate experiments. Panel B. Northern analysis of clusterin mRNA expression in the ventral prostate of adult intact rats orally treated for over 1 month (5 times/week, 27 administrations) with vehicle (lane 1), increasing concentrations of Compound A (10, 30, μg/Kg, lane 2 and 3) or finasteride (40 mg/Kg, lane 4). Every lane was loaded with 10 μg of total RNA. The corresponding GAPDH expression and the ethidium bromide staining of the gel are shown below the blot. The blot is representative of two separate experiments.

Figure 6:
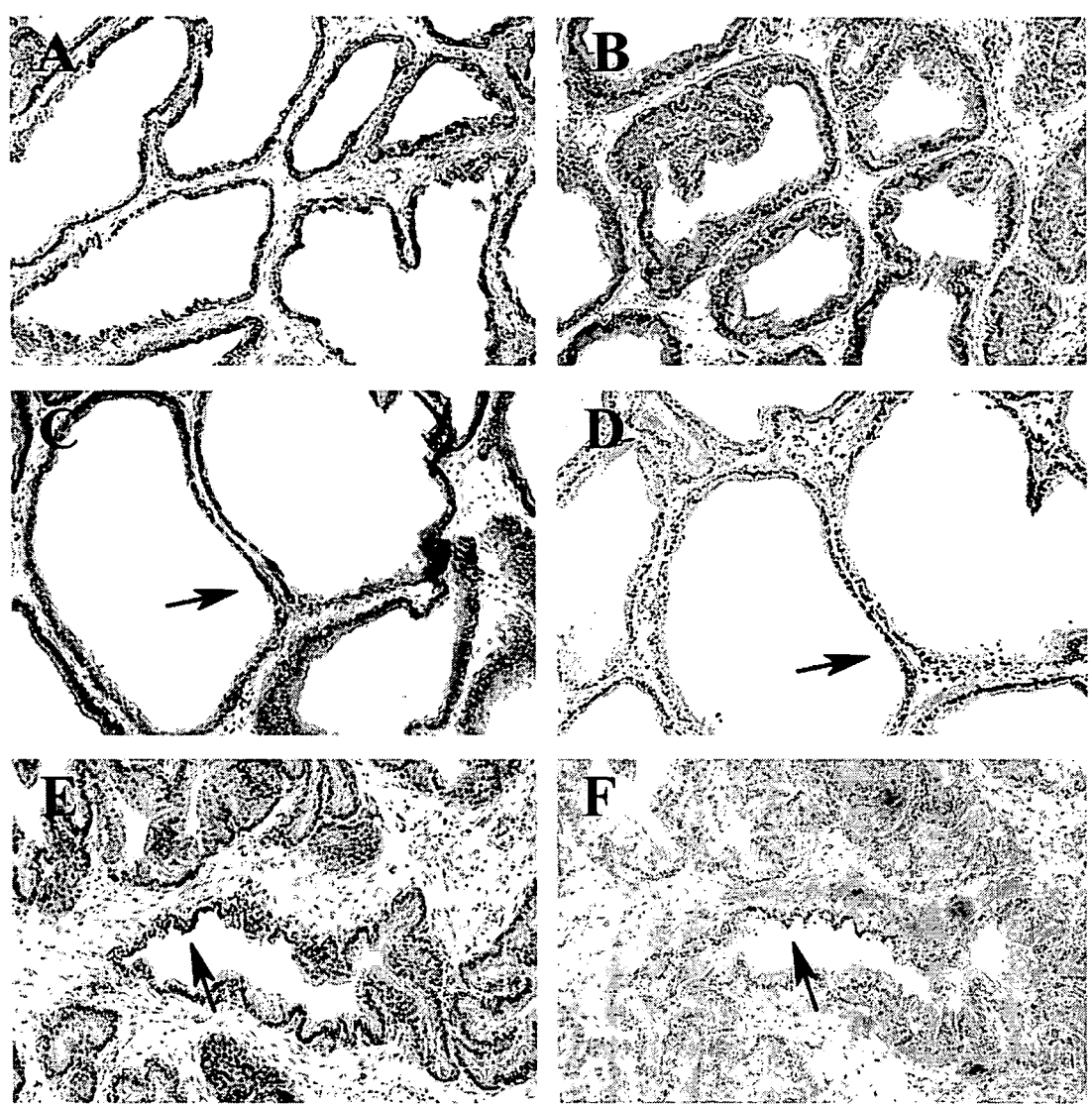
FIG. 6 shows the morphological effects of Compound A on ventral prostate of castrated and T-supplemented rats.

FIG. 6 shows the morphological effects of Compound A on ventral prostate of castrated and T-supplemented rats. Panels A, B, C and E. Representative fields obtained from cross-sections of whole prostate glands immunostained with a monoclonal antibody against rat clusterin and counterstained with haematoxylin. In vehicle-treated rats castrated 4-days earlier, clusterin labelling is detectable in the cytoplasm of the atrophic cuboidal epithelial cells (Panel A, 10×). After two-week T supplementation (Panel B, 10×), almost all the clusterin labelling disappeared. Conversely, clusterin positive cells were still present in rats treated with T and different doses of Compound A (100 μg/Kg, Panel C; 300 μg/Kg, Panel E, black arrows). Panels D and F shows sections consecutive to those in Panel C and E, to highlight DNA fragmentation as assessed by terminal deoxynucleotidyl transferase (TdT)-mediated dUTP nick end-labelling (TUNEL). Two-week treatment (9 administrations) with Compound A (100 μg/Kg, Panel D; 300 μg/Kg, Panel F) induced massive apoptosis in the majority of epithelial and stromal cells. Note (black arrows), that all the clusterin-positive cells were undergoing apoptosis, while also a consistent portion of clusterin unlabeled cells shows nuclear fragmentation.

Figure 7:
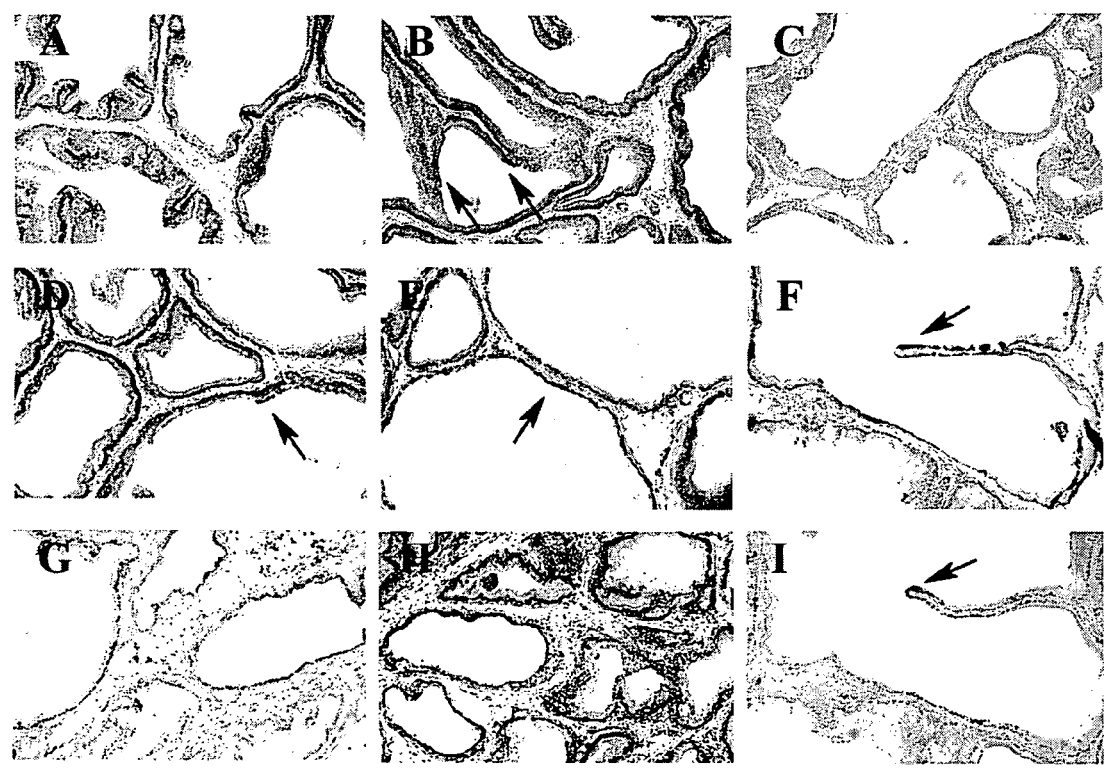
FIG. 7 shows the morphological effects of Compound A and finasteride on the prostate of intact, adult rats.

FIG. 7 shows the morphological effects of Compound A and finasteride on the prostate of intact, adult rats. Panels A, B, D, E, F and H. Representative fields obtained from cross-sections of whole prostate glands immunostained with a monoclonal antibody against rat clusterin and counterstained with haematoxylin. In Panel A (10×) the primary antibody was omitted. Panel B (10×) shows that in untreated adult rats only few, scanty epithelial cells were labelled in some glands (black arrows). Conversely, in prostate glands from rats treated with increasing concentrations of Compound A cuboidal epithelial cells showing the hallmark of atrophy were dose-dependently stained for clusterin (see black arrows, 10 μg/Kg, Panel D; 30 μg/Kg, Panel E, 100 μg/Kg, Panel F, 10×). Similar results were obtained with finasteride (40 mg/Kg, Panel H, 10×). Panels C, G and I shows serial, consecutive slices to those depicted in Panel B, D and F, respectively, to highlight DNA fragmentation as assessed by terminal deoxynucleotidyl transferase (TdT)-mediated dUTP nick end-labelling (TUNEL). Note (black arrows), that all the clusterin-positive cells were undergoing apoptosis, while also a consistent portion of clusterin unlabeled cells shows nuclear fragmentation.

Figure 8:
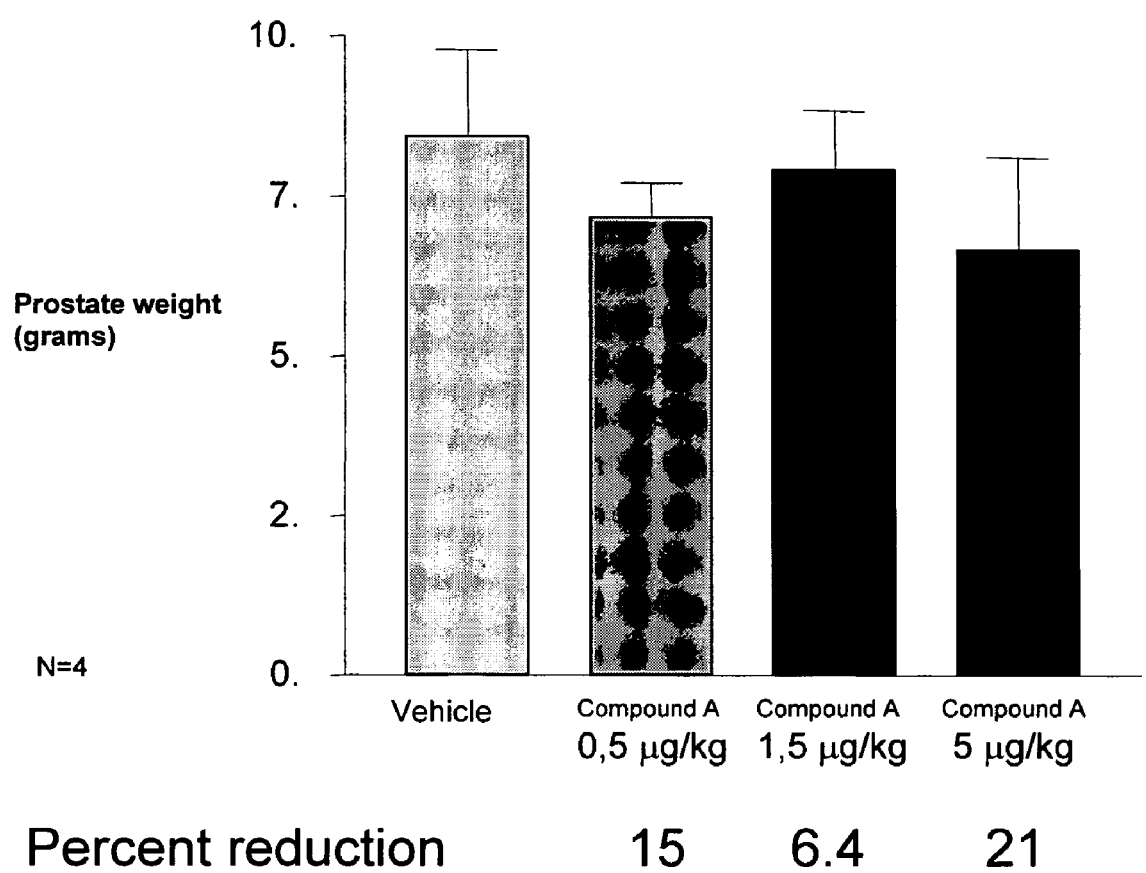
FIG. 8 shows results of a chronic toxicity study in dogs.

FIG. 8 shows results of a chronic toxicity study in dogs. A clear reduction of prostate weight is shown after 9 months of treatment with Compound A relative to placebo.

Figure 9:
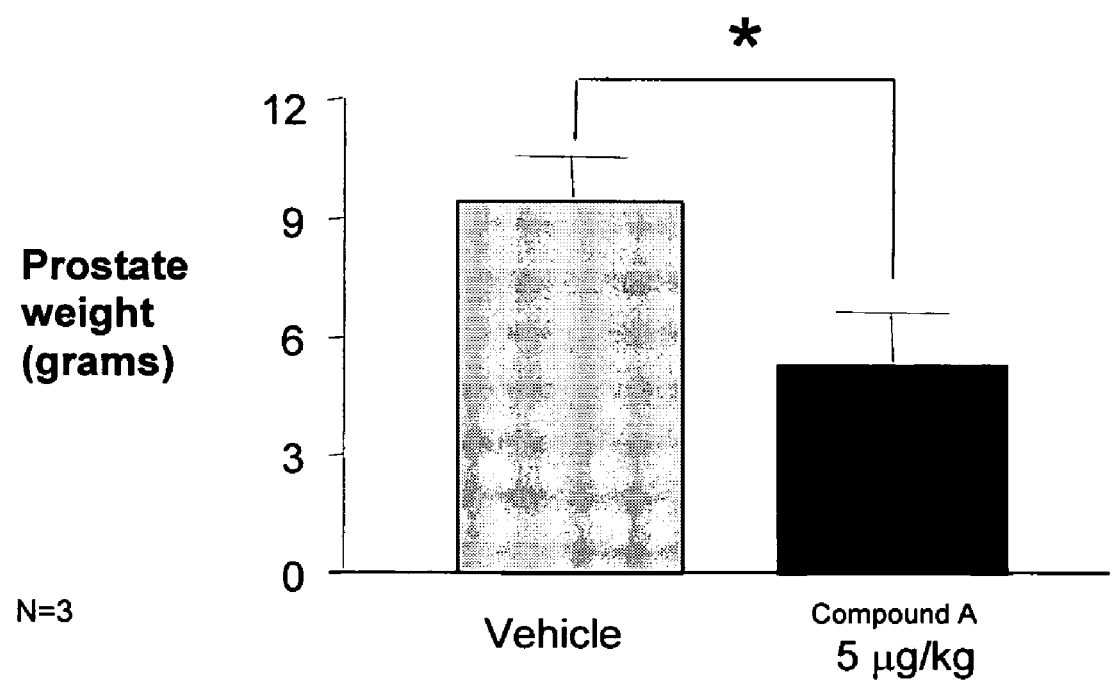
FIG. 9 shows results of a chronic toxicity study in dogs.

FIG. 9 shows results of a chronic toxicity study in dogs. A reduction of prostate weight after recovery from treatment with Compound A relative to placebo.

Figure 10:
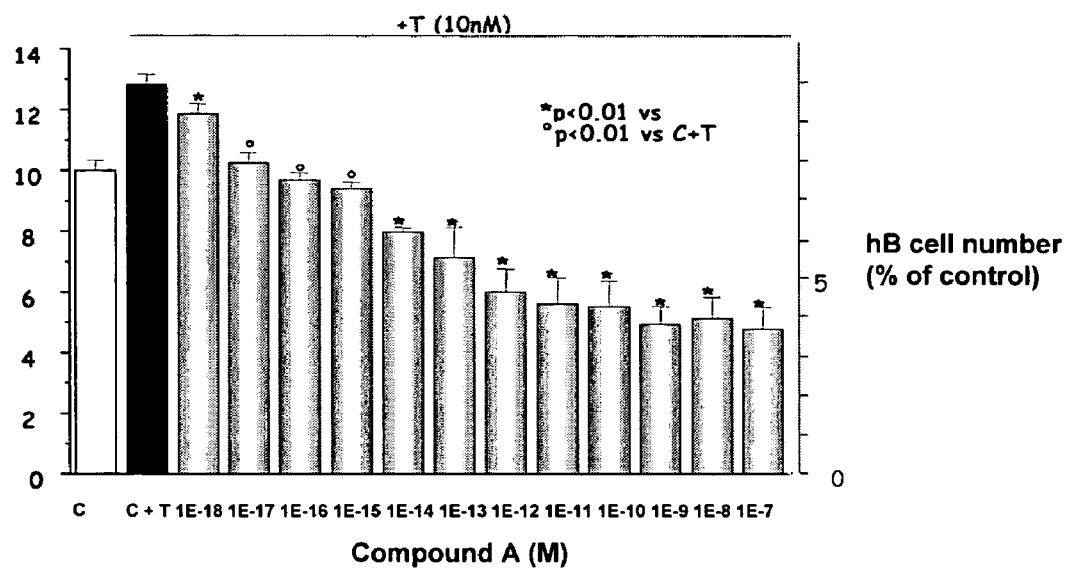
FIG. 10 shows the effect of Compound A on testosterone-stimulated bladder cell growth. "hB"=human bladder
Figure 11:
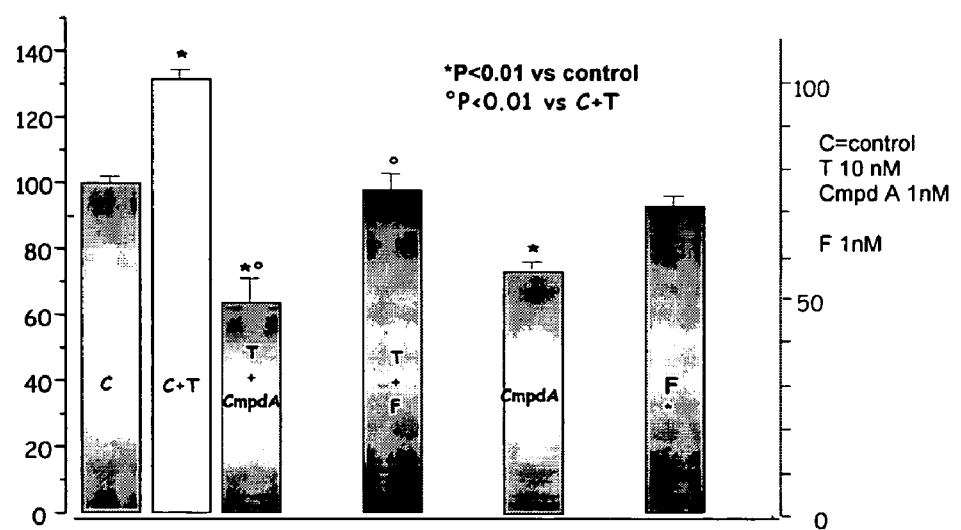
FIG. 11 shows the effect of Compound A and other comparator compounds on stimulated and basal bladder cell growth. "T 10 nM"=testosterone; F 1 nM"=finasteride.

FIG. 10 shows the effect of Compound A on testosterone-stimulated bladder cell growth. "hB"=human bladder FIG. 11 shows the effect of Compound A and other comparator compounds on stimulated and basal bladder cell growth. "T 10 nM"=testosterone; F 1 nM"=finasteride.

Figure 12:
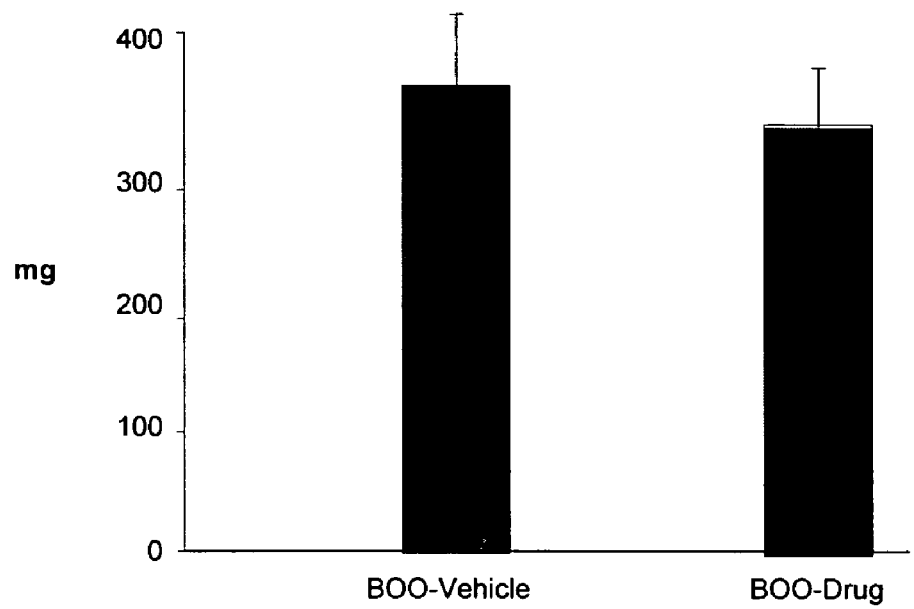
FIG. 12 shows the effect of a vitamin D compound on bladder weight.

FIG. 12 shows the effect of a vitamin D compound on bladder weight.

Figure 13:
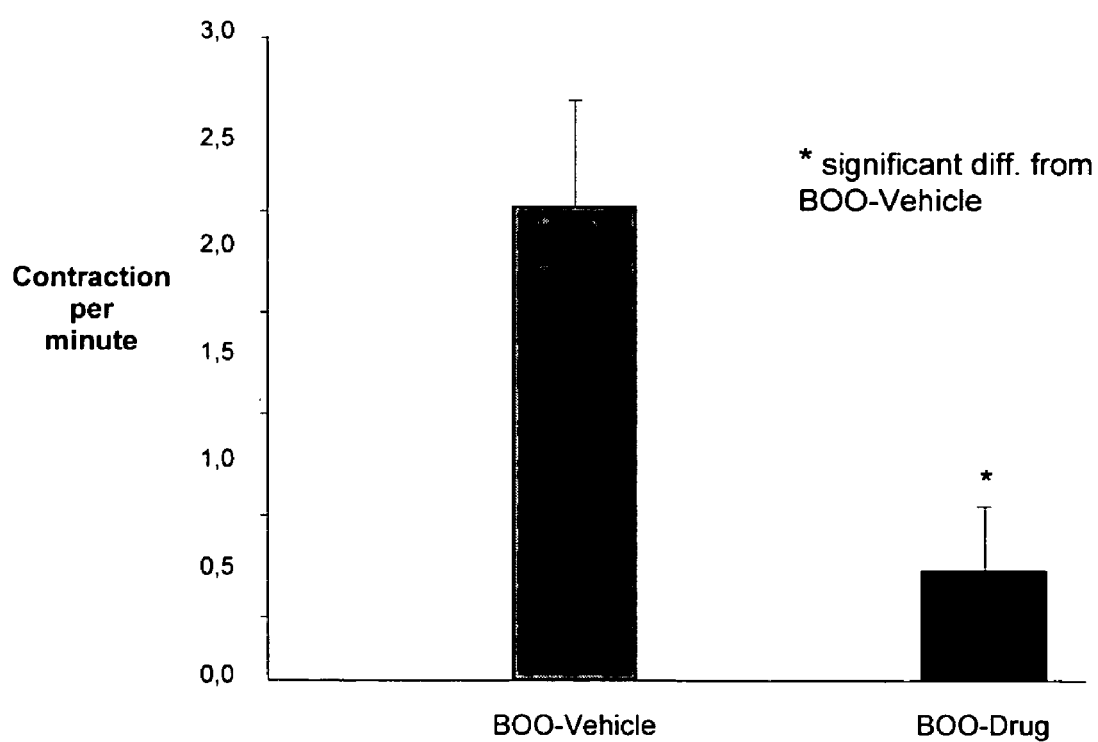
FIG. 13 shows the effect of a vitamin D compound on spontaneous non-voiding contraction frequency.

FIG. 13 shows the effect of a vitamin D compound on spontaneous non-voiding contraction frequency.

Figure 14:
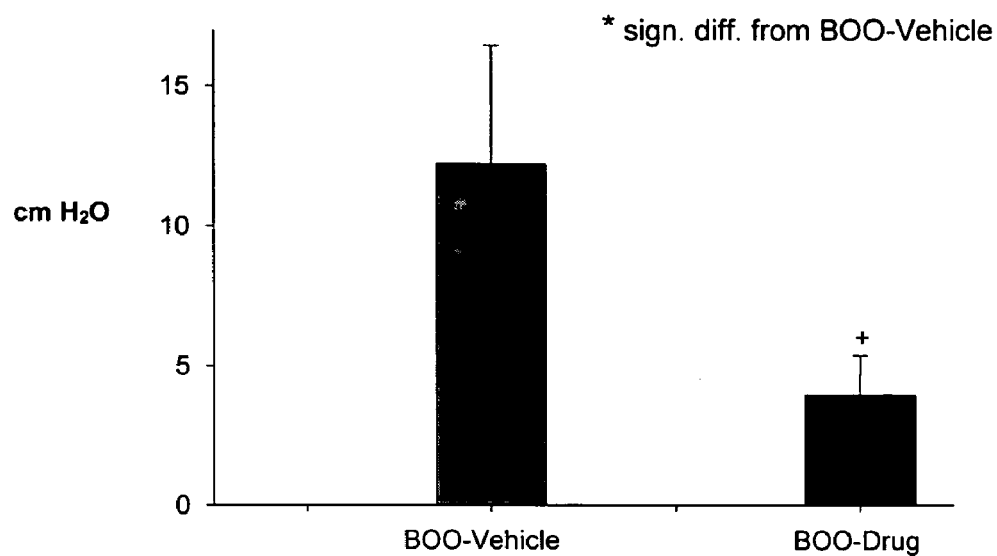
FIG. 14 shows the effect of a vitamin D compound on spontaneous non-voiding contraction amplitude.

FIG. 14 shows the effect of a vitamin D compound on spontaneous non-voiding contraction amplitude.

Figure 15:
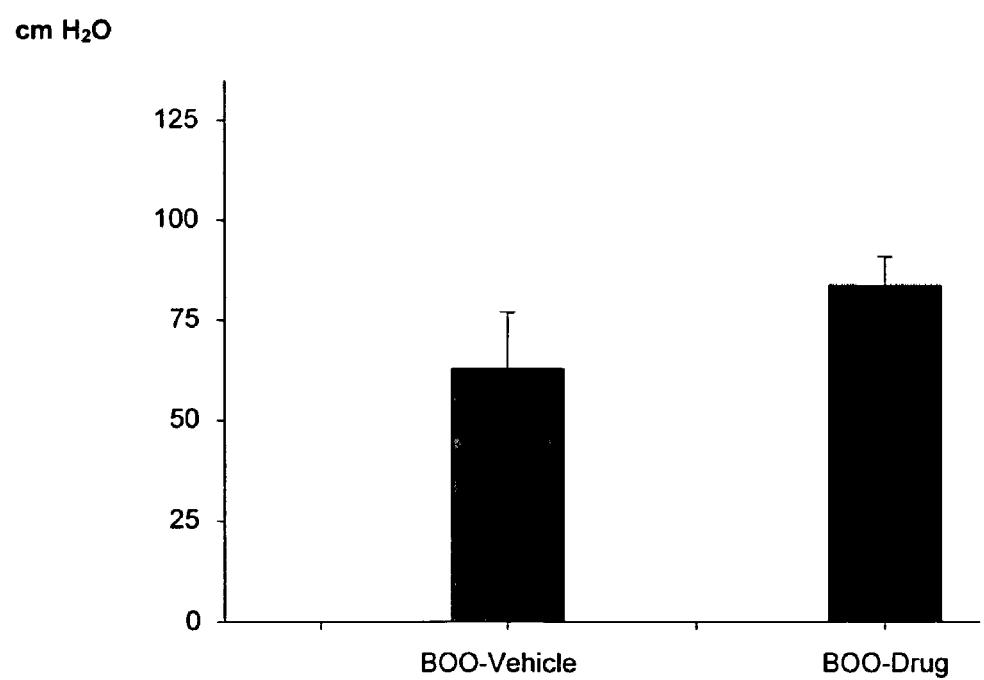
FIG. 15 shows the effect of a vitamin D compound on micturition pressure.

FIG. 15 shows the effect of a vitamin D compound on micturition pressure.

Figure 16:
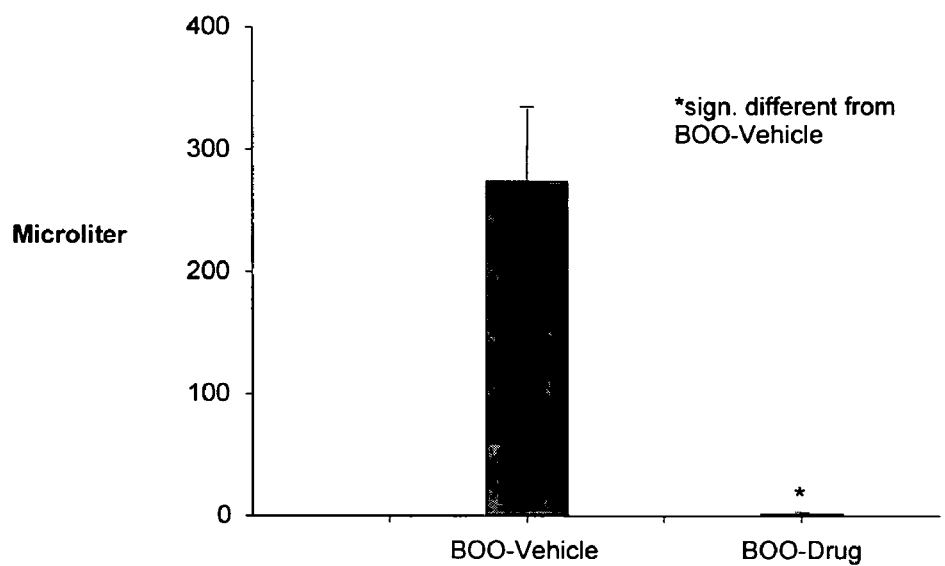
FIG. 16 shows the effect of a vitamin D compound on residual urine.

FIG. 16 shows the effect of a vitamin D compound on residual urine.

Figure 17:
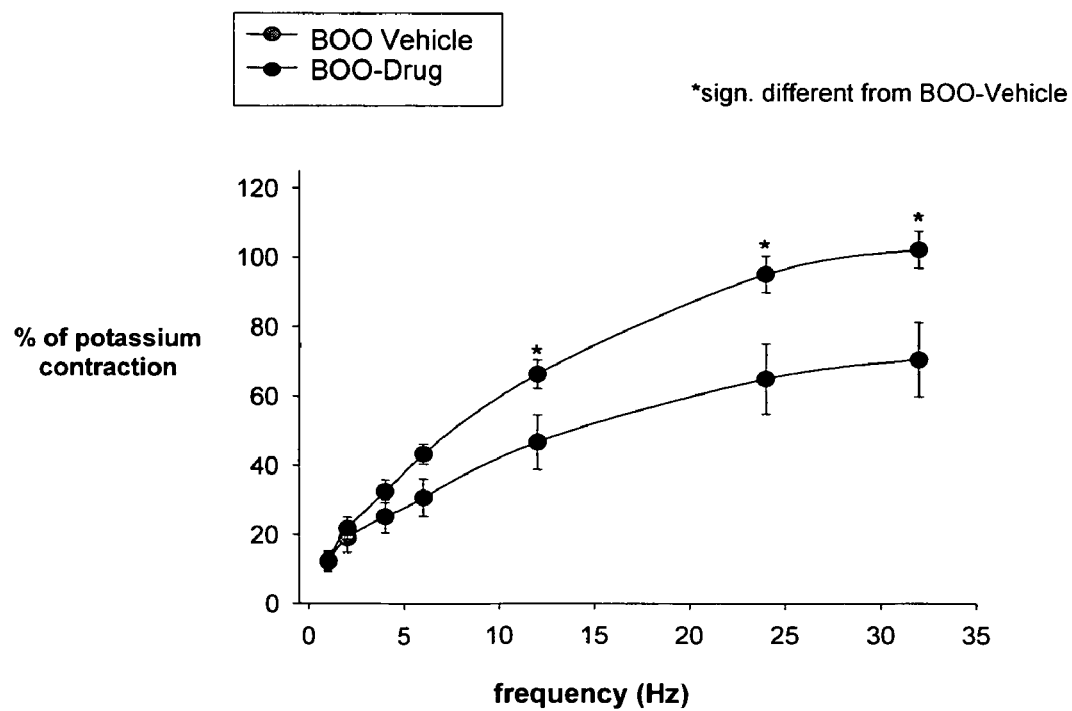
FIG. 17 shows the effect of a vitamin D compound on the contractile response of bladder strips to EFS (Electrical Field Stimulation).

FIG. 17 shows the effect of a vitamin D compound on the contractile response of bladder strips to EFS (Electrical Field Stimulation).

Example 1

Effects of Compound A on BPH Cells in vitro

Material and Methods

Materials

Minimum Essential Medium (MEM), DMEM-F12 1:1 mixture, Ham's F12 medium, phosphate buffered saline (PBS), bovine serum albumin (BSA) fraction V, glutamine, geneticine, collagenase type IV, vitamin $D_3$, testosterone (T), dihydrotestosterone (DHT), cyproterone acetate, β-nicotinamide adenine dinucleotide 3'-phosphate reduced form (NADPH), dithithreitol (DTT), phenylmethylsulfonyl fluoride (PMSF) and a kit for measuring calcemia were purchased from Sigma (St. Louis, Mo.). The protein measurement kit was from Bio-Rad Laboratories, Inc. (Hercules, Calif.). Fetal bovine serum (FBS) was purchased from Unipath (Bedford, UK). Monoclonal anti-rat clusterin antibody (mouse monoclonal IgG) specific for beta-chain was from UPSTATE Biotechnology (Lake Placid, N.Y.). Apop Tag kit for in situ end labelling (ISEL) was from Oncor (MD, USA). CHO 1827 and CHO 1829 were provided by Serono International (Geneva, Switzerland). Instagel plus was purchased from Packard (St Louis, Mo.). Finasteride (pure substance) (17β-(N,t-butyl)carbamoyl-4-aza-5α-androst-1-en-3-one) was a kind gift from Merck Sharp & Dohme Reaserch Laboratories (Rahway, N.J.). Bicalutamide was a kind gift from AstraZeneca (AstraZeneca, Milan, Italy). Analogue 1-α-fluoro-25-hydroxy-16,23E-diene-26, 27-bishomo-20-epi-cholecalciferol (Compound A) was provided by Bioxell (Bioxell, Milan, Italy). Keratinocyte growth factor (KGF) was from Pepro Tech EC (London, England) and insulin-like growth factor-I, human, [Des(1-3)IGF-I] was purchased from GroPep Limited (Adelaide, Australia). In Situ Cell Death Detection Kit POD for terminal deoxynucleotidyl transferase (TdT) mediated dUTP nick end-labelling (TUNEL) were from Roche Diagnostics Corporation (Indianapolis, Ind.). Plastic ware for cell cultures was purchased from Falcon (Oxnard, Calif.). Disposable filtration units for growth media preparation were purchased from PBI International (Milan, Italy). Lipofectamine 2000 and Opti-MEM I Medium for luciferase transfection were from Invitrogen, Life Technologies (San Giuliano Milanese, Milan, Italy). Thin-layer chromatography (TLC) silica plates were obtained from Merck (Darmstad, Germany). Testosterone enanthate (T enanthate) was from Geymonat (Anagni, Italy). Coat-A-Count® Total Testosterone detection kit was purchased from Medical System (Genova Struppa, Italy). Rat luteinizing hormone (rLH) [$^{125}$I] assay systems were from Amersham Pharmacia Biotech (Piscataway, N.J.).

BPH Cells

Human BPH cells, prepared, maintained and used as previously described in Crescioli C, et al. *Journal of Clinical and Endocrinology Metabolism* (2000) 85 p 2576-2583, were obtained from prostate tissues derived from 5 patients, who underwent suprapubic adenomectomy for BPH, after informed consent and approval by the Local Ethical Committee. Patients did not receive any pharmacological treatment in the 3 months preceding surgery.

5α Reductase-Transfected CHO-1827 and CHO-1829 Cell Lines

CHO-1827 and CHO-1829 cells, transfected with 5α reductase type 1 (5αR-1) or type 2 (5αR-2), respectively (see Steers W. *Urology* (2001) 58 p 17-24), were maintained in Ham's F12 medium supplemented with 5% FCS.

AR-Transfected PC3 Cell Line

Human prostate adenocarcinoma PC3 cells, stably transfected with the plasmid p5HbhAR-A containing human androgen receptor (hAR) as previously described (see Bonaccorsi L, et al. *Endocrinology* (2000) 141 p 3172-3182), were grown in 75 cm$^2$ culture flasks in Ham's F-12 medium containing 50 μg/ml geneticihe, 10% FCS, penicillin (100 U/ml) and streptomycin (100 mg/ml).

BPH Tissue

Prostatic tissues for binding assay were obtained from patients who underwent suprapubic adenomectomy for BPH. No pharmacological treatment was performed in the 3 months preceding surgery. After surgery, the tissues were immediately placed in liquid nitrogen and stored at −80° C. until processing.

Rat Tissues

Rat ventral prostate glands were rapidly excised out, weighed and quickly frozen in dry ice. Immunohistochemistry experiments were performed in 14 μm-thick contiguous cryostatic sections for direct comparison of tissue morphology, clusterin expression and apoptosis localization by TUNEL. For total RNA extraction and Western blot analysis, rat ventral prostates from 4 to 6 animals were pooled.

BPH Cell Proliferation Assay

For all cell proliferation assay, $4 \times 10^4$ BPH cells were seeded onto 12-well plates in their growth medium, starved in red- and serum-free medium containing 0.1% BSA for 24 h, and then treated with specific stimuli for 48 h. Cells in phenol red- and serum-free medium containing 0.1% BSA were used as controls. Thereafter, cells were trypsinized, and each experimental point was derived from hemocytometer counting, averaging at least six different fields for each well, as previously reported (see Crescioli C, et al. *Journal of Clinical and Endocrinology Metabolism* (2000) 85 p 2576-2583). Experiments were performed using increasing concentrations ($10^{-18}$-$10^{-7}$M) of calcitriol or Compound A with or without a fixed concentration of T (10 nM), KGF or Des(1-3)IGF-I (10 ng/ml). Growth assays were also carried out using a fixed concentration of androgens (10 nM) with or without Compound A (1 nM, 10 nM) or the anti-androgens finasteride (F, 1 nM) and cyproterone acetate (Cyp, 100 nM). Growth assays were also performed using a fixed concentration of T (10 nM) or GFs (10 ng/ml) with or without Compound A (10 nM). In the same experiment, each experimental point was repeated in triplicate or quadruplicate and experiments were performed 3 times. Results are expressed as % variation (mean±SEM) over the maximal T or GF-induced stimulation.

In Situ End Labeling (ISEL)

ISEL was performed onto BPH cells using Apop Tag in situ apoptosis detection kit peroxydase following the manufacturer's instruction. Cells were incubated with T (10 nM), KGF (10 ng/ml) or Des(1-3)IGF-I (10 ng/ml) with or without Compound A (10 nM). The percentage of apoptotic cells (the number of stained cells divided by the total number of cells) was calculated in at least five separate fields per slide in five different slides. Results are expressed as mean±SEM from three separate experiments.

5α Reductase Inhibition Test

5α reductase inhibition assay was performed using CHO 1827 cells, transfected with 5αR-1, or CHO 1829 cells, transfected with 5αR-2, as described (see Guarna A, et al. *Journal of Medicinal Chemistry* (2000) 43 3718-3735.).

Compound A was added in a concentration range from $10^{-9}$ to $10^{-5}$ M, using finasteride as a control inhibitor in each experiment.

Binding Assay

Binding assay on cytosol fractions of BPH fragments were carried out as previously reported (see Crescioli C et al. *Endocrinology* (2003) 144 p 3046-3057), (final protein concentration: 1.8 mg/ml). Incubations of cytosolic fractions were carried out with increasing concentration (0.125, 0.25, 0.5, 1 nM) of [$^3$H]-R1881 (specific activity: 83.5 Ci/mmol) in the absence or in the presence ([$^3$H]-R1881:1 nM) of increasing concentrations of cold R1881 ($10^{-10}$-$10^{-6}$ M), DHT ($10^{-10}$-$10^{-6}$ M), T ($10^{-10}$-$10^{-6}$ M), bicalutamide ($10^{-10}$-$10^{-4}$ M), and Compound A ($10^{-10}$-$10^{-4}$ M). To prevent R1881 binding to progesterone receptor, 1 µM triamcinolone acetonide was added to each tube. Separation of bound and unbound ligand was performed as previously described (see Crescioli C et al. *Endocrinology* (2003) 144 p 3046-3057). Protein content was determined by the known method of Bradford, using BSA as a standard.

Luciferase Assay

PC3 cells stably transfected with human AR were plated in 24-well plates at a density of $2 \times 10^4$ in Ham's F12 plus 10% FCS. After 24 hours, the cells were transfected with 750 ng/well of pLSPP plasmid containing the wilde-type sequence configuration of the MMTV-LTR linked to the firefly luciferase gene (see Pazzagli M. et al. *Analytical Biochemistry* (1992) 204 p 315-323.), using Lipofectamine 2000 (1 mg/ml) according to the manufacturer's instructions. After 48 h, the cells were incubated with DHT ($10^{-12}$-$10^{-6}$ M) or bicalutamide ($10^{-9}$-$10^{-5}$M), in the presence of 3 nM of DHT, and with equimolar concentration of Compound A for 18 h. Steroids and Compound A analogue were dissolved in ethanol. Transfected cells incubated with ethanol only served as positive controls.

The Luciferase assay was performed with a Berthold luminometer according to the manufacturer's instructions (Luciferase Assay System, Promega, Milan, Italy). The cells were lysed directly in the plate with 200 µl of lysis buffer. Luciferase activity was measured on 20 µl of cell lysate for 10 s after addition of 100 µl of luciferine. Total protein measurement was performed on 20 µl of cell lysate. At least three independent assays were done in duplicate.

Results

Incubation of BPH cells with increasing concentrations of calcitriol or Compound A inhibits cell growth (FIG. 1 panel A). Both compounds inhibited dose-dependently cell proliferation. ALLFIT (see De Lean A, et al. *American Journal of Physiology* (1978) 235 p E97-E102) analysis indicated that, although maximal inhibition of calcitriol and Compound A ("Cmpd A" in the Figures) was not statistically significantly different ($I_{max}$=43±1%), their relative potency was, Compound A being several log units more effective than calcitriol (–log $IC_{50}$ Compound A=15.8±0.3 vs –log $IC_{50}$ calcitriol=10.2±0.6, P<0.005).

BPH cell proliferation was significantly increased (P<0.01) by testosterone (T) (156±8%), and growth factors (GF), such as Des(1-3)IGF-I (194±6%) or KGF (183±5%). When cell growth was stimulated for 48 h with T or GFs (FIG. 1, panel B) the inhibitory effect of Compound A was even more pronounced ($I_{max}$=66.6±7.3%). Mathematical modelling (see De Lean A, et al. *American Journal of physiology* (1978) 235 p E97-E102) of inhibition curves indicated that Compound A was more potent in BPH cells stimulated with T (–log $IC_{50}$s=16.4±0.6) than with the other two growth factors (–log $IC_{50}$s=12.7±0.6, and –log $IC_{50}$=14.2±0.6 for Des(1-3)IGF-I and KGF, respectively; P<0.0001).

Compound A (1 nM) antagonized not only T- but also DHT-stimulated BPH cell proliferation to an extent similar to the AR antagonist cyproterone acetate (Cyp, 100 nM; FIG. 2 panel A and B). Conversely, the 5α-reductase inhibitor finasteride (F, 1 nM) antagonized only T-induced cell growth (FIG. 2 panel A). In addition, Compound A reduced growth even in androgen-unstimulated cells (FIG. 2, panel A).

To evaluate potential anti-androgenic properties of Compound A, in addition to BPH cell growth inhibition, we investigated its interaction with the AR. First, we ruled out the possibility that Compound A binds to the AR by performing competition studies in human BPH homogenates, using the synthetic androgen [$^3$H]-R1881 as labelled ligand. LIGAND analysis (see Munson P J et al. Analytical Biochemistry (1980) 107 p 220-239.) of the data indicated that unlabeled R1881, DHT, T, and the AR antagonist bicalutamide completely displaced [$^3$H]-R1881 binding (Table I). Conversely, Compound A did not compete for [$^3$H]-R1881 binding at any concentration tested (Table I). These results were confirmed and extended using a luciferase reporter gene assay. In PC3 cells expressing the full length AR coupled to a luciferase report gene, DHT stimulated a dose-dependent increase in luciferase activity ($EC_{50}$=2±1.3 nM, panel A), while bicalutamide inhibited DHT-stimulated activity ($IC_{50}$=194±80 nM, panel B). In this system, increasing concentration of Compound A neither stimulated nor inhibited AR-mediated luciferase activity increase (FIG. 3). Finally to verify whether or not Compound A interacts with the formation of DHT, the active metabolite of T, we performed experiments in CHO cells transfected with type 1 and type 2 5α reductase. Results were compared to those obtained with finasteride (F). While F inhibited T conversion into DHT with the expected $IC_{50}$s, ($IC_{50}$ for 5α reductase type 1=659±100 nM and $IC_{50}$ for 5α reductase type 2, =53.7±11 nM, n=3), Compound A did not interfere with either isoenzyme up to the micromolar range (data not shown).

TABLE I

Affinity constants of androgen agonists (R1881, DHT, T), antagonist (bicalutamide) and Compound A in human BPH homogenates as detected by [$^3$H]R1881 binding.

| AR Ligand | Affinity constants ($K_d$ nmol/L) |
| --- | --- |
| R1881 | 0.16 ± 0.06 |
| DHT | 0.07 ± 0.03 |
| T | 1.89 ± 0.94 |
| Bicalutamide | 159 ± 82 |
| Compound A | >100000 |

The effect of Compound A in BPH cells was, at least in part, due to activation of programmed cell death as detected by ISEL (n=3, Table II). The percentage of apoptotic nuclei dramatically increased (270%) after a 48 h exposure to 10 nM Compound A (P<0.01 vs control). Conversely, treatment with T (10 nM), or GFs (10 ng/ml) significantly (P<0.01) reduced the number of apoptotic BPH cells as compared to untreated cells (Des(1-3)IGF-I=–42%; KGF=–54%; T=–27%). However, even in the presence of GFs or T, Compound A induced a sustained (more than 250%) and significant (P<0.01) increase in the number of ISEL-positive BPH cells.

TABLE II

Effect of Compound A (10 nM), GFs (10 ng/ml) or T (10 nM) on DNA fragmentation in BPH cells. Apoptotic index (%) represents the number of stained nuclei, as detected by ISEL, over BPH cells in each of at least 5 separate fields per slide. Results are expressed as mean ± SEM in three separate experiments. Compound A is able to induce apoptosis in untreated BPH cells as well as in BPH cells simultaneously incubated with GFs or T (a: P < 0.01 vs control; b: P < 0.01 vs Compound A-treated cells; c: P < 0.01 vs GF- or T-treated cells).

Apototic index (%)

|  | Control | Compound A |
| --- | --- | --- |
| Control | 18.55 ± 0.8 | 68.44 ± 1.26[a] |
| Des(1-3)IGF-I | 10.69 ± 0.6[a] | 45.85 ± 0.66[a,b,c] |
| KGF | 8.5 ± 0.42[a] | 44.46 ± 0.57[a,b,c] |
| T | 13.56 ± 0.72[a] | 49.06 ± 1.87[a,b,c] |

Example 2

Anti-proliferative Properties of Compound A in in vivo Models of Prostate Growth Animal Protocols Male Sprague Dawley rats (28 days old) were purchased from Charles River Laboratories (Calco, Lecco, Italy). All animal experimentation described was conducted in accord with accepted standards of animal care. Castration was performed via the scrotal route under ketamine/xylazine anaesthesia. Three days after castration, rats (5-8 animals per group) were treated or not with T enanthate (30 mg/Kg) in two separate weekly sc injections. Rats were orally treated for 5 days the first week, and 4 days the second week with vehicle (Miyglyol 812), Compound A (10, 30, 100 and 300 µg/Kg) or finasteride (10 and 40 mg/Kg) for a total of 9 administrations, and sacrificed one day later.

Alternatively, intact, adult male Sprague Dawley rats (weight 250 g) were dosed orally with vehicle (Miglyol 812), Compound A (10, 30, 100 and 300 µg/Kg) or finasteride (10 and 40 mg/Kg) 5 days/week for 5 consecutive weeks and for two additional days the $6^{th}$ week, for a total of 27 administrations, unless otherwise specified. Blood for calcium and hormone measurements was obtained at the end of each experimental protocol.

Northern Hybridisation Analysis

Total RNA was extracted using RNAFast from Molecular System (San Diego, Calif.). Blotting, labelling, hybridization conditions and probes (rat clusterin 1.5 Kb full-length cDNA and GAPDH 1.2 Kb full-length cDNA) were performed according to the reported procedures (Bettuzzi et al, *Biochemical Journal*, (1989), 257, p 293-296 and Marinelli et al, *Biochemistry and Cell Biology*, (1994), 72, p 515-521). Quantitation of the autoradiograms was obtained by densitometric scanning using an LKB Ultrascan XL densitometer.

Immunohistochemistry

All the cryostatic sections obtained from controls and treated rats were processed in parallel as previously described (Astancolle et al, *Journal of Endocrinology*, (2000), 167, p 197-204). For every experimental condition, 3 alternate sections from 3 different rat prostates were examined. Negative controls, made by excluding the specific antibody from the reaction, showed no specific staining. Counterstaining was performed with haematoxylin, and cover slips were mounted with Eukitt (O. Kindler GmbH & Co, Germany). Digital high-magnification colour images were acquired by a CCD camera through the microscope.

In situ DNA Fragmentation Analysis (TUNEL)

DNA fragmentation in prostate cryostatic sections, assessed by terminal deoxynucleotidyl transferase (TdT)-mediated dUTP nick end-labelling (TUNEL), was performed using the In Situ Cell Death Detection Kit (POD, Roche) as recommended by the manufacturer. TUNEL positive apoptotic nuclei were documented by digital high-magnification colour images acquired by a CCD camera through the microscope. Counterstaining was performed with eosin, and cover slips were mounted with Eukitt (O Kindler GmbH & Co, Germany).

Calcium Measurements

Serum calcium levels were measured with a commercially available colorimetric assay (Sigma), according to the manufacturers' instructions.

Testosterone and rLH Measurement

Serum levels of T and rLH hormones were determined by commercially available radioimmunoassay kits, according to the manufacturers' instructions. To measure serum T in rats, samples were first added to 4 volumes of diethyl ether, mixed by gentle inversion for 15 min and then centrifuged for 5 min at 2000 rpm. The aqueous phase was frozen in dry ice and the organic phase was recovered and evaporated to dryness under a nitrogen stream. The dried extract was reconstituted in the assay buffer as follows: (1 vol: 1 vol) in intact rat, and (4 vol: 1 vol) in castrated rats.

Statistical Analysis

Statistical analysis was performed by one-way ANOVA and paired or unpaired Student's t tests, when appropriate. Binding data were analysed using the computerized program LIGAND (Munson et al, *Analytical Biochemistry*, (1980), 107, p 220-139).

The computer program ALLFIT (DeLean et al, *American Journal of Physiology*, (1978), 235, p E97-E102) was used for the analysis of sigmoid dose-response curves to obtain estimates of half-maximal inhibition values ($IC_{50}$) and half-maximal stimulatory values ($EC_{50}$) as well as maximal inhibitory ($I_{max}$) and stimulatory ($E_{max}$) effects. Data were expressed as (mean±SEM).

Results

To test the anti-proliferative properties of Compound A in in vivo models of prostate growth, castrated and intact rats were orally treated with increasing concentrations of Compound A (10-300 µg/Kg) or finasteride (F) (10, 40 mg/Kg). As shown in FIG. 4, panel A, castration dramatically reduced ventral prostate weight, while a two-week treatment with testosterone (T) enanthate (30 mg/Kg) not only completely restored, but further stimulated its growth. Compound A, at any dose tested, completely blunted T-stimulated prostate over-growth, reducing ventral prostate weight below that of untreated rats. Similar results were obtained with finasteride (10, 40 mg/Kg). A one-month treatment of intact adult rats with Compound A significantly decreased ventral prostate weight, with a maximal reduction (30%) at the highest dose tested (300 µg/Kg). At this dose, the inhibitory effect of Compound A on prostate growth was comparable to that induced by 10 or 40 mg/Kg finasteride (FIG. 4, panel B). In all the experimental protocols, oral administration of different doses of Compound A caused a very modest hypercalcemia only at the highest dose tested (300 µg/Kg) (Table III). No other discernible side effects were observed.

TABLE III

Calcemia (mg/dl) in T-replaced castrated rats after different doses (10, 30, 100, 300 µg/Kg) of Compound A. Compound A never changed calcium serum levels in castrated rats replaced with T enanthate (30 mg/ Kg/week) as compared to controls. Similar results were obtained in intact rats (not shown). Results represent the mean ± SEM of rats/ group.

|  | calcemia |
|---|---|
| Control | 10.2 ± 0.16 |
| Compound A 10 µg/Kg | 10.16 ± 0.24 |
| Compound A 30 µg/Kg | 9.87 ± 0.15 |
| Compound A 100 µg/Kg | 10.55 ± 0.18 |
| Compound A 300 µg/Kg | 10.85 ± 0.1 |

To better understand the molecular mechanisms underlying Compound A-induced prostate weight reduction, the expression of clusterin gene and protein and the morphological hallmarks of apoptosis were evaluated by terminal deoxynucleotidyl transferase (TdT) mediated dUTP nick end-labelling (TUNEL). Clusterin is an ubiquitous product gene, strictly related to cell cycle arrest and atrophy, the expression of which is down regulated by androgens. FIG. 5 panel A, shows the prostatic expression of clusterin mRNA, as detected by Northern analysis, in orchidectomized rats supplemented or not supplemented with T. Castration dramatically up-regulated clusterin mRNA abundance, while this effect was completely reverted by a two-week administration of T. The simultaneous treatment with different concentrations of Compound A (300 and 100 µg/Kg) or F (40 mg/Kg) partially blunted the T-induced down-regulation of clusterin gene expression. In intact rats (FIG. 5 panel B), a one-month administration of different concentrations of Compound A (30 and 100 µg/Kg) induced a sustained increase in clusterin gene expression in the prostate, comparable, or even higher, than that induced by 40 mg/Kg F.

The local expression of clusterin in the prostate of orchidectomized rats is shown in FIG. 6. Castration induced a marked and widespread atrophy in the prostate gland, and nearly all the cuboidal epithelial cells facing the gland lumen were clusterin positive (panel A). T-replacement (panel B) reverted the morphological hallmarks of atrophy and consistently reduced clusterin staining. Such an effect was prevented by the simultaneous administration of Compound A (panels C and E). Panels D and F show TUNEL results in sections adjacent to those shown in panels C and E. Compound A treatment (100 µg/Kg, panel D and 300 µg/Kg, panel F) induced an evident nuclear fragmentation in epithelial and stromal cells, and apoptosis was detectable in both clusterin positive and negative cells. The first two panels of FIG. 7 show the morphology of the prostate gland of an intact rats processed for clusterin detection, with (panel A) or without (panel B) the omission of the primary antibody. Note that clusterin labelling is almost absent in the prostate of untreated adult rats (panel B), as it is nuclear fragmentation (TUNEL, panel C). Conversely, treatment with different doses of Compound A induced clusterin expression (panels D-F) and apoptosis (C, G and I). Panel F shows, for comparison, the effect of finasteride (40 mg/Kg) on clusterin positivity in the prostate gland.

To rule out the possibility that Compound A reduced in vivo prostate growth by interfering with pituitary or testis function, rat luteinizing hormone (rLH) and T serum levels were measured in castrated and intact rats. As expected (Table IV, panel A), castration significantly reduced T while it increased rLH serum levels. T enanthate (30 mg/Kg) administration (two weeks) completely reverted the effect of orchidectomy. Oral treatment with Compound A (100 and 300 µg/Kg) of T-replaced castrated rats did not significantly affect rLH or T serum levels. Similar results were obtained in intact rats (Table IV, panel B). In fact, chronic administration (1 month) of Compound A (10, 30, 100 µg/Kg) or F (40 mg/Kg) to intact rats did not modify rLH and T serum levels.

TABLE IV rLH (ng/ml) and T (nM) serum levels in T-replaced castrated (panel A) or intact (panel B) rats after treatment with different doses of Compound A. Panel A. Castration signficantly reduced serum T ($*P < 0.01$ vs control) while it increased serum rLH ($*P < 0.05$ vs control). After treatment with T enanthate (30 mg/Kg/week) rLH and T serum levels were restored. Compound A at all the doses tested did not significantly affect either rLH or T serum levels. Panel B chronic administration (1 month) of F (40 mg/Kg) or Compound A (10, 30 and 100 µg/Kg) did change neither rLH nor T serum levels in intact rats.

|  | rLH | T |
|---|---|---|
| Panel A | | |
| control (intact rats) | 2.36 ± 0.46 | 11.5 ± 2.44 |
| Castrated | 20.64 ± 6* | 0.9 ± 0.32* |
| castrated + T-replaced | 2.08 ± 0.36 | 21.25 ± 4.12 |
| castrated + T-replaced + Compound A 100 µg/Kg | 1.8 ± 0.2 | 11.13 ± 1.02 |
| castrated + T-replaced + Compound A 300 µg/Kg | 3.15 ± 0.65 | 15.73 ± 2.75 |
| Panel B | | |
| control (intact rats) | 2 ± 0.16 | 11.98 ± 2.87 |
| Finasteride | 2.2 ± 0.4 | 18.11 ± 3.23 |
| Compound A 10 µg/Kg | 2.22 ± 0.25 | 19.13 ± 3.83 |
| Compound A 30 µg/Kg | 2.32 ± 0.36 | 9.39 ± 2 |
| Compound A 100 µg/Kg | 1.96 ± 0.13 | 11 ± 2.14 |

This study demonstrates that Compound A reduces prostate size in intact rats to an extent similar to finasteride. In addition, as finasteride, Compound A abolishes the in vitro and in vivo proliferative activity of testosterone. However, at variance with finasteride, Compound A does not inhibit type-1 or type-2 5α-reductase activity and can counteract not only T but even DHT induced BPH cell growth. These anti-androgenic properties of Compound A are independent from interaction with the AR, as shown by the failure of Compound A to bind to the AR, and to act as AR agonist or antagonist in AR-transfected PC3 cells. Furthermore, Compound A does not affect sex hormone secretion because, in the rat, gonadotropin and T plasma levels were unchanged by daily administration of Compound A for up to one month. Hence, Compound A acts downstream the AR receptor-ligand interaction. Without wishing to be bound by theory this action most probably occurs via the disruption of testosterone-growth factor cross talk.

Very low concentrations of Compound A were able to completely antagonize not only T-stimulated BPH cell proliferation, but also proliferation induced by the two most important intra-prostatic growth factors: IGF-I and KGF. In addition, even in the presence of T or GFs, Compound A induced apoptosis in BPH cells. The Compound A-induced death program was evident also in the prostate of both intact and T-supplemented orchidectomized rats and was characterized by the diffuse appearance of DNA fragmentation with a concomitant increase in clusterin gene and protein expression. Clusterin is a protein tightly regulated in the prostate by androgens (Bettuzzi et al, *Biochemical Journal*, (1989), 257, p 293-296). Although clusterin function is still not well understood, it is markedly up-regulated in conditions of gland atrophy (Bettuzzi et al, *Oncogene*, (2002), 21, p 4328-4334 and Bettuzzi et al, *Journal of Endocrinology*, (1992), 132, p 361-367) and apoptosis (Leskov et al, *Journal of Biological Chemistry*, (2003), 278, p 11590-11600). Thus, clusterin induction by Compound A treatment is consistent with the capacity of this compound to inhibit proliferation and induce apoptosis in prostate cells.

In conclusion, this study indicates that Compound A is effective in reducing prostate cell growth in different experimental models.

Example 3

Reduction of Prostate Weight in Healthy Dogs Treated with Compound A

A 9-month toxicity study was carried out in four groups of male beagle dogs, which were treated by daily oral gavage with 0.5 µg, 1.5 µg and 5 µg/kg body weight/day of Compound A (in vehicle Miglyol 812) or with vehicle alone. This treatment was followed by a 2-month recovery period for the group receiving the highest dose, 5 µg, after which prostate weights was measured. In addition to entirely favourable toxicity data, a lower prostate weight was observed at the end of treatment with Compound A (see FIG. 8) and after recovery (see FIG. 9). The results after recovery were analysed statistically via a one-tailed Student's t test and were found to be significantly different between Compound A and vehicle (P<0.05). These results further demonstrate the ability of Compound A to reduce prostate size in vivo.

Example 4

Oral Dosage Form Soft Gelatin Capsule

A capsule for oral administration is formulated under nitrogen in amber light from 0.01 to 25.0 mg of Compound A in 150 mg of fractionated coconut oil (e.g., Miglyol 812), with 0.015 mg butylated hydroxytoluene (BHT) and 0.015 mg butylated hydroxyanisole (BHA), filled in a soft gelatin capsule.

The capsule is prepared by the following process:

1. BHT and BHA are suspended in fractionated coconut oil (e.g., Miglyol 812) and warmed to around 50° C. with stirring, until dissolved.
2. Compound A is dissolved in the solution from step 1. at 50° C.
3. The solution from step 2. is cooled to room temperature.
4. The solution from step 3. is filled into soft gelatin capsules.

All manufacturing steps are performed under a nitrogen atmosphere and protected from natural light.

Example 4A

Oral Dosage Form Soft Gelatin Capsule

A capsule for oral administration is formulated under nitrogen in amber light: 150 µg of Compound A in 150 mg of fractionated coconut oil (Miglyol 812), with 0.015 mg butylated hydroxytoluene (BHT) and 0.015 mg butylated hydroxyanisole (BHA), filled in a soft gelatin capsule.

Example 4B

Oral Dosage Form Soft Gelatin Capsule

A capsule for oral administration is formulated under nitrogen in amber light: 75 µg of Compound A in 150 mg of fractionated coconut oil (Miglyol 812), with 0.015 mg butylated hydroxytoluene (BHT) and 0.015 mg butylated hydroxyanisole (BHA), filled in a soft gelatin capsule.

Example 5

Reduction in Prostate Weight in Human Clinical Trials

A randomised double blind placebo controlled parallel group study was performed to determine the effect of Compound A (1-alpha-fluoro-25-hydroxy-16,23E-diene-26,27-bishomo-20-epi-cholecalciferol) in patients with BPH.

The principal inclusion criterion was that male patients be diagnosed with BPH and have prostate volume >40 ml as determined by transrectal ultrasound (TRUS).

Statistical methods: primary efficacy analyses were planned on Per-Protocol (PP) Population and, as support, the same analyses were to be done on Intent-to-treat population. Patients evaluatable for the Per-Protocol analysis were all randomized patients compliant to protocol criteria who completed the whole course of study without major protocol violations and have valid assessments of prostate volume. Patients valid for intent-to-treat (ITT) population were all randomized patients who received at least one dose of trial medication and for whom the prostate volume at baseline and at 12 weeks visit were available.

All patients randomized who took at least one dose of study drug were evaluated for safety analysis.

The treatment group comparability was assessed at baseline for all patients with descriptive meaning. The data were processed by the Chi-Square test for the categorical variables, and by the ANOVA model for the continuous variables.

Descriptive statistics were calculated by means of usual methods: mean, standard deviation, minimum and maximum values on continuous variables, and absolute and relative frequencies for categorical ones. Descriptive statistics were done per treatment and per visit/weeks.

Centers with Less than 4 Patients were Pooled.

The primary efficacy variable was the percentage change of prostate volume, measured by centralized MRI axial scanning. An ANOVA model was used for the analysis, with treatment and center as fixed effects.

Study participants received 150 µg capsule (as per Example 4A with drug omitted in the case of placebo) once daily in the morning. The treatment period was 12 weeks. The number of patients involved was as follows:

|  | Compound A | Placebo | Total |
| --- | --- | --- | --- |
| Randomised patients | 57 | 62 | 119 |
| Complete patients | 56 (98.3%) | 60 (96.8%) | 116 (97.5%) |
| Discontinued or lost to follow-up | 0 | 2 (3.2%) | 2 (1.7%) |
| Unsatisfactory therapeutic effect | 1 (1.8%) | 0 | 1 (0.8%) |

Percentage Change in Prostate Volume Measured by Axial Scanning

The percentage change in prostate volume in the PP population was −1.89±5.2 in the Compound A group vs 4.99+5.99 in placebo group with a significant p vale of <0.0001 in favour of Compound A. The estimate of difference between treatments (Compound A minus placebo) was −7.24 with 95% confidence limit of −9.54 and −4.94. The centre effect was also significant (p=0.0176). The same analysis performed on the ITT population confirmed the results (p=0001), that is that Compound A was more effective than placebo in reducing the prostate volume.

In patients with a baseline prostate volume >=80 ml the difference between treatment groups (p=<0.0001) was clearer in comparison with patients with a baseline prostate volume <60 ml (p=0.0320) especially in the PP population.

In patients with age between 61-70 years the difference between treatments, always in favour of Compound A, was more evident than with respect to older patients (age >70 years). In fact in the ITT population, the difference between treatments in patients with age >70 had a significance of p=0.0540 vs p=<0.0001 for the other classes of patients.

Responders

The proportion of responders observed with Compound A was 27.5%, in the PP population, with an unchanged proportion of 65% and only a 7.5% of patients not responder. In placebo group the class of responders was null, in fact patients were equitably separated in unchanged and not responder (50% in each class). The Chi-Square test comparing proportions confirmed the results observed in the primary efficacy variable, p=<0.0001, that is Compound A was more effective than placebo in reduction of prostate volume.

In the ITT population the results were confirmed, the proportion of responders in the Compound A group being 28.8%, with a chi-square p-value of <0.0001 between treatments.

The mean reduction of prostate volume vs baseline in responder patients was −6.88±2.5, in the PP population, while the mean difference in unchanged patients is −0.35±2.3 in the Compound A group vs 0.40±2.0 in Placebo group. For non responder patients the mean difference was 3.93±0.8 in the Compound A group vs 7.48±4.9 in Placebo group that confirms the greater efficacy of Compound A in controlling and reducing prostate volume.

Percentage Change of Prostate Volume Measured by Centralized Paraxial and Transitional Scanning The supportive analyses on paraxial and transitional acquisition confirmed the results obtained on axial scanning. In particular, in the PP population, for paraxial acquisition the percentage change was −1.30±6.9 in the Compound A group vs 2.57±6.8 in placebo group, p=0.0172; while for transitional scanning the percentage change was −0.22±9.6 for Compound A group vs 6.18±10.9 for Placebo group, p=0.0028. Also in the ITT population there was a significant difference between treatments in favour of Compound A, in reduction of prostate volume.

Serum Total PSA and Hormone Levels

The PSA mean change in the Compound A group was 0.23±1.3 vs 0.43±1.7 in placebo group, for PP population. No significant difference was observed between treatments (p=0.2722).

Also for testosterone, in PP population, there was no significant difference between groups (p=0.2150), with mean change 0.07±1.5 in the Compound A group vs 0.22±1.4 in Placebo group.

There was no difference between treatment groups for dihydrotestosterone (p=0.7257−PP population), with an observed mean change in PP population of −30.77±227.71 in the Compound A group vs −166.76±490.26 in the Placebo group.

There was no difference in LH hormone (p=0.9320−PP population), with a mean change in Compound A of −0.02±1.7 vs −0.00±1.8 in Placebo group for PP population.

The mean changes observed in PSA and in hormone levels was around zero, except for DHT, Compound A does not modify the hormone levels.

The same results were confirmed in the ITT population.

Safety

The number of patients with at least one adverse event was 31 (17 in the Compound A group, 14 in placebo group); no patient dropped out due to adverse events, and only one patient in Placebo group experienced a serious adverse event: an acute colecystitis, solved with hospitalization.

The number of patients with adverse events related to Compound A treatment was 3 (5.26%), while the number of patients with adverse events related to treatment was 6 (9.68%) in the Placebo group. The events related to Compound A were: dizziness, headache, libido decrease and hot flushes, while the events related to Placebo were: urine phosphate increase, headache, syncope, libido decrease (3 patients), hypercalciuria, erectile dysfunction and hot flushes.

The calciuria values monitored over the course of the study in the Compound A group did not differ significantly from the Placebo group.

Conclusion

In this short proof of concept study for effect of Compound A on prostatic size in patients with BPH, the drug proved to be efficacious. The analysis of the primary variable of the study, namely the evaluation of the prostatic size, showed significant difference between Compound A and placebo, thus confirming that the tested drug is able to arrest the progression of the disease. The safety profile was good, there was no different incidence of adverse events between Compound A and placebo, and no severe adverse event was reported in Compound A group. The tested drug was devoid of any antiandrogenic effects, had no effect on PSA levels, and had no significant effect on the calcium homeostasis.

Example 6

The Activity of Compound A on the Growth and Function of Bladder Cells

Compound A has been shown to be effective in inhibiting the basal and testosterone-stimulated growth of bladder cells. This activity, never reported before, is dose-dependent with a $1.6 \pm 7 \times 10^{-15}$ for 1-alpha-fluoro-25-hydroxy-16,23e-diene-26,27-bishomo-20-epi-cholecalciferol ("Compound A"/"Cmpd A" in the figures) (on stimulated cells) (see FIG. 10 and FIG. 11).

This effect was significantly greater than that of the anti-androgen finasteride widely used in the treatment of uro-genital diseases (FIG. 11).

Example 7

The Effect of Compound A on Bladder Dysfunction in a Bladder Outlet Obstruction Model Experimental 1. Materials 1.1. Animals:

Female Sprague-Dawley rats, weighing 200-250 g 1.2. Grouping

Group A: BOO rats, treated with Compound A over 2 weeks, beginning at day 1 after creation of the obstruction (n=12)

Group B: BOO rats, treated with vehicle over 2 weeks, beginning at day 1 after creation of the obstruction (n=12)

Group C: Sham operated rats, treated with Compound A over 2 weeks, beginning at day 1 after surgery (n=12)

1.3. Studies:

a) Cystometry (~18 hours after last administration of the drug/vehicle, 12 hours after removal of the obstructing ligature) under conscious conditions.

b) Measurements of bladder weight c) In vitro investigations

2. Methods 2.1. Bladder Outlet Obstruction (BOO):

The bladder and urethrovesical junction were exposed through a lower abdominal midline incision. A 0.9 mm metal rod was placed alongside the proximal urethra and a 3-0 silk ligature was tied tightly around the urethra and the rod, which was consequently be removed. Sham surgery was be performed accordingly, without placing the ligature. After 13 days the ligature was be removed and a catheter was be inserted into the bladder dome and tunneled subcutaneously.

2.2. Cystometry

The following morning after insertion of the catheter, the cystometric investigation was performed without any anesthesia or restraint in a metabolic cage. The amount of voided urine was measured by means of a fluid collector, connected to a force displacement transducer. The bladder was continuously filled with saline at room temperature. The catheter was also connected to a pressure transducer. After a stabilization period of 30-60 minutes, when reproducible voiding patterns are achieved, the following parameters were recorded over a period of 30 minutes: Basal bladder pressure, micturition pressure, threshold pressure, micturition interval and volume, and non-voiding contractions. The amount of residual urine was investigated manually 3 times, at the end of the cystometry. Bladder capacity was calculated based on the measured values.

2.3. In vitro Investigations 2.3.1. Preparations.

After completion of the cystometries, the rats were sacrificed by carbon monoxide asphyxiation followed by exsanguination. The abdomen was accessed through a lower midline incision whereafter the symphysis was opened. The bladder was carefully dissected free, and immediately placed in chilled Krebs solution, and strip preparations were dissected.

2.3.2 Recording of Mechanical Activity.

The bladder and urethra were separated at the level of the bladder neck, and semicircular strips were prepared from the middle third of the detrusor (1×2×5 mm). All preparations were used immediately after removal.

The strips were transferred to 5 ml tissue baths containing Krebs solution. The Krebs solution was maintained at 37° C. and bubbled continuously with a mixture of 95% $O_2$ and 5% $CO_2$, resulting in a pH of 7.4. The strips were suspended between two L-shaped hooks by means of silk ligatures. One hook was connected to a movable unit allowing adjustment of passive tension, and the other to a Grass FT03C (Grass Instruments Co, MA, USA) force transducer. Isometric tension was recorded using a Grass polygraph (7D). After mounting, the strips were stretched to a passive tension of 4 mN (the same tension for all preparations) and allowed to equilibrate for 45-60 min before further experiments were performed.

2.3.3. Electrical Field Stimulation

Electrical field stimulation (EFS) was accomplished by means of two platinum electrodes placed on either side of the preparations, and was performed using a Grass S48 or S88 stimulator, delivering single square wave pulses at selected frequencies. The train duration was 5 s, the pulse duration 0.8 ms, and the stimulation interval 2 min. The polarity of the electrodes was shifted after each pulse by means of a polarity changing unit.

2.3.4 Procedure

Each experiment was started by exposing the preparations to a high $K^+$ (124 mM) Krebs solution until two reproducible contractions are obtained. Then the following experiments were carried out:

a) Electrical stimulation of nerves was performed and frequency-response relations obtained, in the presence and absence of atropine.

b) Concentration-response curves were constructed for carbachol and ATP

Results

The validated bladder outlet obstruction rat model described above was used to test the ability of Compound A to control and treat bladder dysfunction. The objective was to evaluate whether a vitamin D3 analogue (1-alpha-fluoro-25-hydroxy-16,23e-diene-26,27-bishomo-20-epi-cholecalciferol—compound "A") at the dose of 150 µg/Kg/daily) can prevent bladder hypertrophy and bladder dysfunction such as bladder overactivity.

In this model a ligature was surgically placed around the outlet of the catheterized bladder, so that when the catheter was removed, the bladder experienced increased urethral resistance. The rats underwent continuous cystometry to evaluate bladder function. In addition the contractile properties of isolated bladder preparation in response to nerve stimulation and exogenous stimuli in vitro were investigated under electrical field stimulation (EFS).

The following cystometric parameters were investigated (see FIGS. 12-16):

micturition pressure (the maximum bladder pressure during micturition), bladder capacity (residual volume after voiding plus the volume of saline infused to induce the void)

micturition volume (volume of the expelled urine)

residual urine (bladder capacity minus micturition volume) and frequency and amplitude of spontaneously occurring changes intravesical pressure (non-voiding contractions).

In this model the analogue under evaluation had a beneficial effect on bladder function. This effect was evident in the normal bladder and is maintained in bladder outlet obstruction. In particular significant differences versus vehicle were observed in:
spontaneous non-voiding contraction frequency and amplitude (FIGS. 13 and 14);
residual urine (absent with Compound A, FIG. 16);
micturition pressure (FIG. 15);

In addition a beneficial effect on bladder function has been confirmed in the in vitro tests:
K response;
response to EFS (FIG. 17);
response to carbachol.

Finally a slight decrease in bladder weight was observed with Compound A (FIG. 12).

These data demonstrate the use of Compound A (in the dose range from 50 µg to 300 µg—equivalent to approximately 0.725 to 5 µg/kg of body mass in humans) in the prevention and treatment of bladder dysfunction, eg overactive bladder, such as is, for example, demonstrated in patients with BPH.

Abbreviations
T testosterone
DHT dihydrotestosterone
GF growth factor
BPH benign prostatic hyperplasia
PP per-protocol
ITT intent-to-treat
ANOVA Analysis of Variance
TRUS Transrectal ultrasound
BOO Bladder Outlet Obstruction
AR Androgen receptors
PSA Prostate Specific Antigen Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims that follow.

Incorporation By Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims.

The invention claimed is:

1. A method for treating benign prostatic hyperplasia in a patient in need of such treatment comprising administering to said patient a therapeutically effective amount of 1-alpha-fluoro-25-hydroxy-16,23E-diene-26,27-bishomo-20-epi-cholecalciferol or a pharmaceutically acceptable salt or ester thereof.

2. A method for treating benign prostatic hyperplasia, in a patient in need of such treatment comprising administering to said patient a therapeutically effective amount of 1-alpha-fluoro-25-hydroxy-16,23E-diene-26,27-bishomo-20-epi-cholecalciferol or a pharmaceutically acceptable salt or ester thereof, sequentially or simultaneously in separate or combined pharmaceutical formulations, with a second BPH-active agent.

3. A method according to claim 2 wherein the second BPH-active agent is an alpha-adrenergic receptor blocking agent.

4. A method according to claim 3 wherein the alpha-adrenergic receptor blocking agent is selected from terazosin, doxazosin, tamsulosin and silodosin, AIO-8507L and RBx-2258.

5. A method according to claim 2 wherein the second BPH-active agent is a 5 alpha-reductase inhibitor.

6. A method according to claim 5 wherein the 5 alpha-reductase inhibitor is selected from finasteride and dutasteride.

7. A method according to claim 1 wherein the 1-alpha-fluoro-25-hydroxy-16,23E-diene-26,27-bishomo-20-epi-cholecalciferol, or pharmaceutically acceptable salt or ester thereof, is provided in unit dose form.

8. A method according to claim 2 wherein the 1-alpha-fluoro-25-hydroxy-16,23E-diene-26,27-bishomo-20-epi-cholecalciferol, or pharmaceutically acceptable salt or ester thereof, is provided in unit dose form.

9. A method according to claim 7 wherein the unit dose of 1-alpha-fluoro-25-hydroxy-16,23E-diene-26,27-bishomo-20-epi-cholecalciferol is 50 to 150 µg.

10. A method according to claim 8 wherein the unit dose of 1-alpha-fluoro-25-hydroxy-16,23E-diene-26,27-bishomo-20-epi-cholecalciferol is 50 to 150 µg.

11. A method according to claim 1, wherein the treatment occurs without anti-androgenic prostatic and extra-prostatic adverse effects.

12. A method according to claim 2, the treatment occurs without anti-androgenic prostatic and extra-prostatic adverse effects.

13. A method according to claim 1, wherein the treatment occurs without hypercalcemic adverse effects.

14. A method according to claim 2 wherein the treatment occurs without hypercalcemic adverse effects.

15. A method for treating benign prostatic hyperplasia in a patient in need of such treatment comprising administering to said patient a therapeutically effective amount of 1-alpha-fluoro-25-hydroxy-16,23 E-diene-26,27-bishomo-20-epi-cholecalciferol or a pharmaceutically acceptable salt thereof.

16. A method for treating benign prostatic hyperplasia in a patient in need of such treatment comprising administering to said patient a therapeutically effective amount of 1-alpha-fluoro-25-hydroxy-16,23E-diene-26,27-bishomo-20-epi-cholecalciferol or a pharmaceutically acceptable salt thereof sequentially or simultaneously in separate or combined pharmaceutical formulations with a second BPH-active agent.

* * * * *